United States Patent
Gartner et al.

(10) Patent No.: US 8,157,818 B2
(45) Date of Patent: Apr. 17, 2012

(54) INTEGRATED MEDICAL APPARATUS FOR NON-TRAUMATIC GRASPING, MANIPULATING AND CLOSURE OF TISSUE

(75) Inventors: Mark J Gartner, Pittsburgh, PA (US); Brian J Fill, Pittsburgh, PA (US)

(73) Assignee: Ension, Inc., Wexford, PA (US)

( * ) Notice: Subject to any disclaimer, the term of this patent is extended or adjusted under 35 U.S.C. 154(b) by 1642 days.

(21) Appl. No.: 11/458,177

(22) Filed: Jul. 18, 2006

(65) Prior Publication Data

US 2007/0027456 A1 Feb. 1, 2007

Related U.S. Application Data

(60) Provisional application No. 60/704,475, filed on Aug. 1, 2005.

(51) Int. Cl.
*A61B 17/04* (2006.01)
(52) U.S. Cl. .......................................... 606/148
(58) Field of Classification Search .................. 606/113, 606/200, 139–141, 148
See application file for complete search history.

(56) References Cited

U.S. PATENT DOCUMENTS

| | | |
|---|---|---|
| 4,654,594 A | 3/1987 | Sepponen |
| 4,769,620 A | 9/1988 | Nicotra |
| 5,007,426 A | 4/1991 | Le Roux |
| 5,053,041 A | 10/1991 | Ansari et al. |
| 5,108,420 A | 4/1992 | Marks |
| 5,190,541 A | 3/1993 | Abele et al. |
| 5,226,908 A | 7/1993 | Yoon |
| 5,282,844 A | 2/1994 | Stokes et al. |
| 5,306,234 A | 4/1994 | Johnson |
| 5,320,629 A | 6/1994 | Noda et al. |
| 5,376,094 A | 12/1994 | Kline |
| 5,403,311 A | 4/1995 | Abele et al. |
| 5,423,830 A | 6/1995 | Schneebaum et al. |
| 5,562,678 A * | 10/1996 | Booker .................. 606/113 |
| 5,643,255 A | 7/1997 | Organ |
| 5,643,293 A | 7/1997 | Kogasaka et al. |
| 5,709,224 A | 1/1998 | Behl et al. |
| 5,727,569 A | 3/1998 | Benetti et al. |
| 5,735,848 A | 4/1998 | Yates et al. |
| 5,766,216 A | 6/1998 | Gangal et al. |
| 5,766,217 A | 6/1998 | Christy |
| 5,779,716 A | 7/1998 | Cano et al. |
| 5,843,152 A | 12/1998 | Tu et al. |
| 5,873,876 A | 2/1999 | Christy |
| 5,908,435 A | 6/1999 | Samuels |
| 5,921,993 A | 7/1999 | Yoon |
| 5,972,002 A | 10/1999 | Bark et al. |

(Continued)

*Primary Examiner* — Thomas J Sweet
*Assistant Examiner* — Eric Blatt
(74) *Attorney, Agent, or Firm* — Blynn L. Shideler; Krisanne Shideler; BLK Law Group

(57) ABSTRACT

The integrated medical apparatus includes an operator handle end and a multi-prong grasping member positioned within and movable relative to a grasper lumen that extends from the handle end, wherein the grasping prongs are moved between an open and closed position by relative axial movement between the prongs of the grasping member and the grasper lumen. The medical apparatus includes a contractible snare and a plurality of axially moveable snare pushing arms. At least two of the snare pushing arms include a snare holding and release mechanism, wherein the snare pushing arms are configured to advance the snare in an open, encircling position to a final deployed position where the snare can be released through the activation of the holding and release mechanism of the pushing arms, and finally tightened in a conventional fashion, such as pulling on an end of the snare at the handle end.

20 Claims, 21 Drawing Sheets

U.S. PATENT DOCUMENTS

| | | |
|---|---|---|
| 5,976,158 A | 11/1999 | Adams |
| 5,984,917 A | 11/1999 | Fleischman et al. |
| 6,016,452 A | 1/2000 | Kasevich |
| 6,019,722 A | 2/2000 | Spence et al. |
| 6,074,408 A | 6/2000 | Freeman |
| 6,077,261 A | 6/2000 | Behl et al. |
| 6,080,173 A | 6/2000 | Williamson, IV et al. |
| 6,152,144 A | 11/2000 | Lesh et al. |
| 6,152,936 A | 11/2000 | Christy et al. |
| 6,203,541 B1 | 3/2001 | Keppel |
| 6,231,561 B1 | 5/2001 | Frasier et al. |
| 6,241,727 B1 | 6/2001 | Tu et al. |
| 6,248,124 B1 | 6/2001 | Pedros et al. |
| 6,277,065 B1 | 8/2001 | Donofrio |
| 6,280,415 B1 | 8/2001 | Johnson |
| 6,290,674 B1 | 9/2001 | Roue et al. |
| 6,299,612 B1 | 10/2001 | Ouchi |
| 6,315,715 B1 | 11/2001 | Taylor et al. |
| 6,322,494 B1 | 11/2001 | Bullivant et al. |
| 6,328,688 B1 | 12/2001 | Borst et al. |
| 6,334,843 B1 | 1/2002 | Borst et al. |
| 6,336,898 B1 | 1/2002 | Borst et al. |
| 6,340,344 B1 | 1/2002 | Christopher |
| 6,357,100 B2 | 3/2002 | Speller, Jr. et al. |
| 6,416,554 B1 | 7/2002 | Alferness et al. |
| 6,485,407 B2 | 11/2002 | Alferness et al. |
| 6,488,689 B1 | 12/2002 | Kaplan et al. |
| 6,491,706 B1 | 12/2002 | Alferness et al. |
| 6,494,211 B1 | 12/2002 | Boyd et al. |
| 6,503,264 B1 | 1/2003 | Birk |
| 6,506,149 B2 | 1/2003 | Peng et al. |
| 6,514,250 B1 | 2/2003 | Jahns et al. |
| 6,610,072 B1 * | 8/2003 | Christy et al. ............ 606/148 |
| 6,666,861 B1 | 12/2003 | Grabek |
| 6,837,893 B2 * | 1/2005 | Miller ...................... 606/139 |
| 6,986,774 B2 * | 1/2006 | Middleman et al. ....... 606/113 |
| 2001/0039419 A1 | 11/2001 | Franchischelli et al. |
| 2001/0039434 A1 | 11/2001 | Frezier et al. |
| 2001/0039435 A1 | 11/2001 | Roue et al. |
| 2002/0002372 A1 | 1/2002 | Jahns et al. |
| 2002/0022860 A1 | 2/2002 | Borillo et al. |
| 2002/0035374 A1 | 3/2002 | Borillo et al. |
| 2002/0049457 A1 | 4/2002 | Kaplan et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0143326 A1 | 10/2002 | Foley et al. |
| 2003/0023266 A1 | 1/2003 | Borillo et al. |
| 2003/0032952 A1 | 2/2003 | Hooven |
| 2004/0030335 A1 | 2/2004 | Zenati et al. |
| 2005/0277959 A1 | 12/2005 | Cosgrove et al. |
| 2006/0129166 A1 * | 6/2006 | Lavelle .................... 606/113 |

* cited by examiner

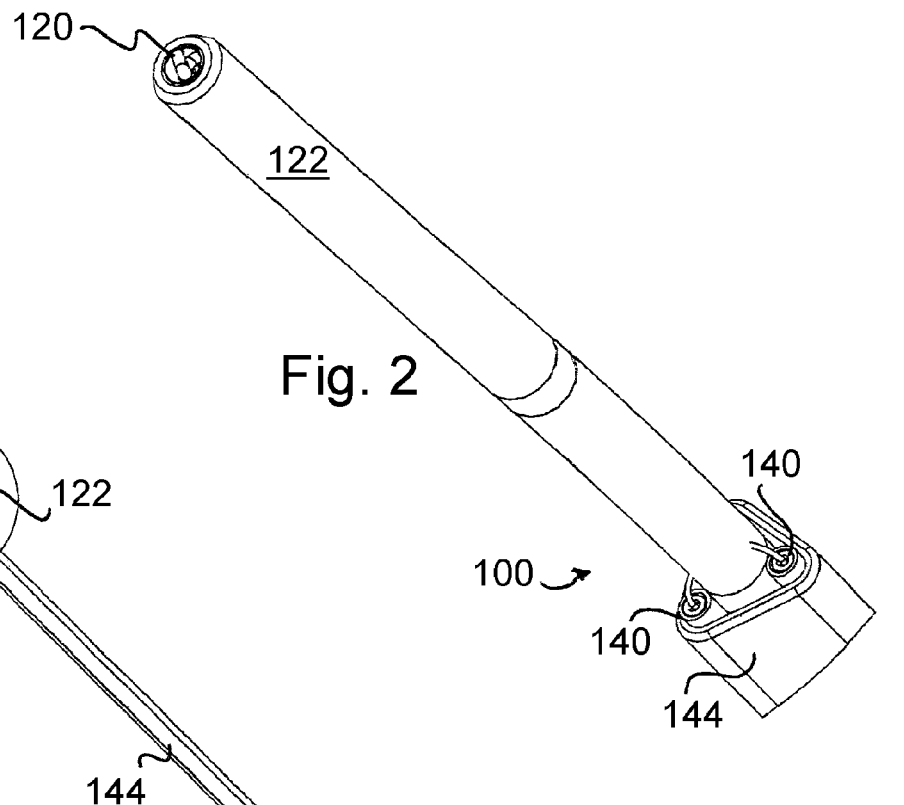
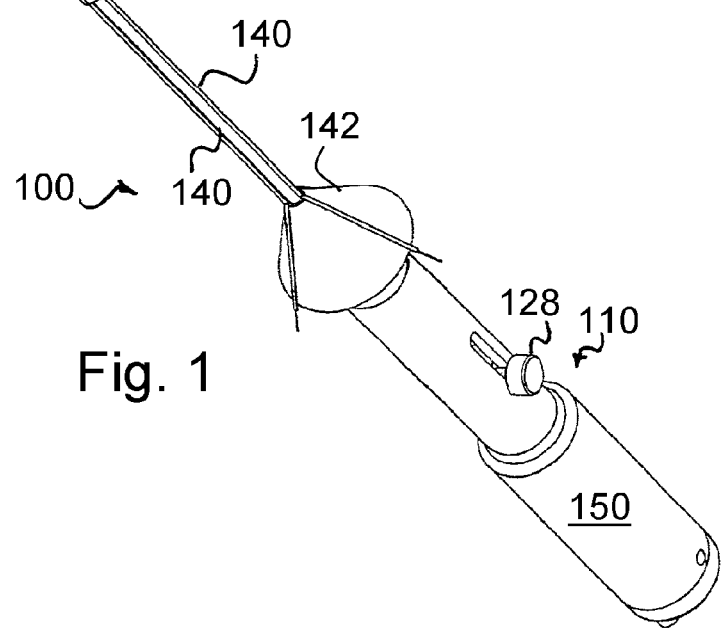
Fig. 2
Fig. 1

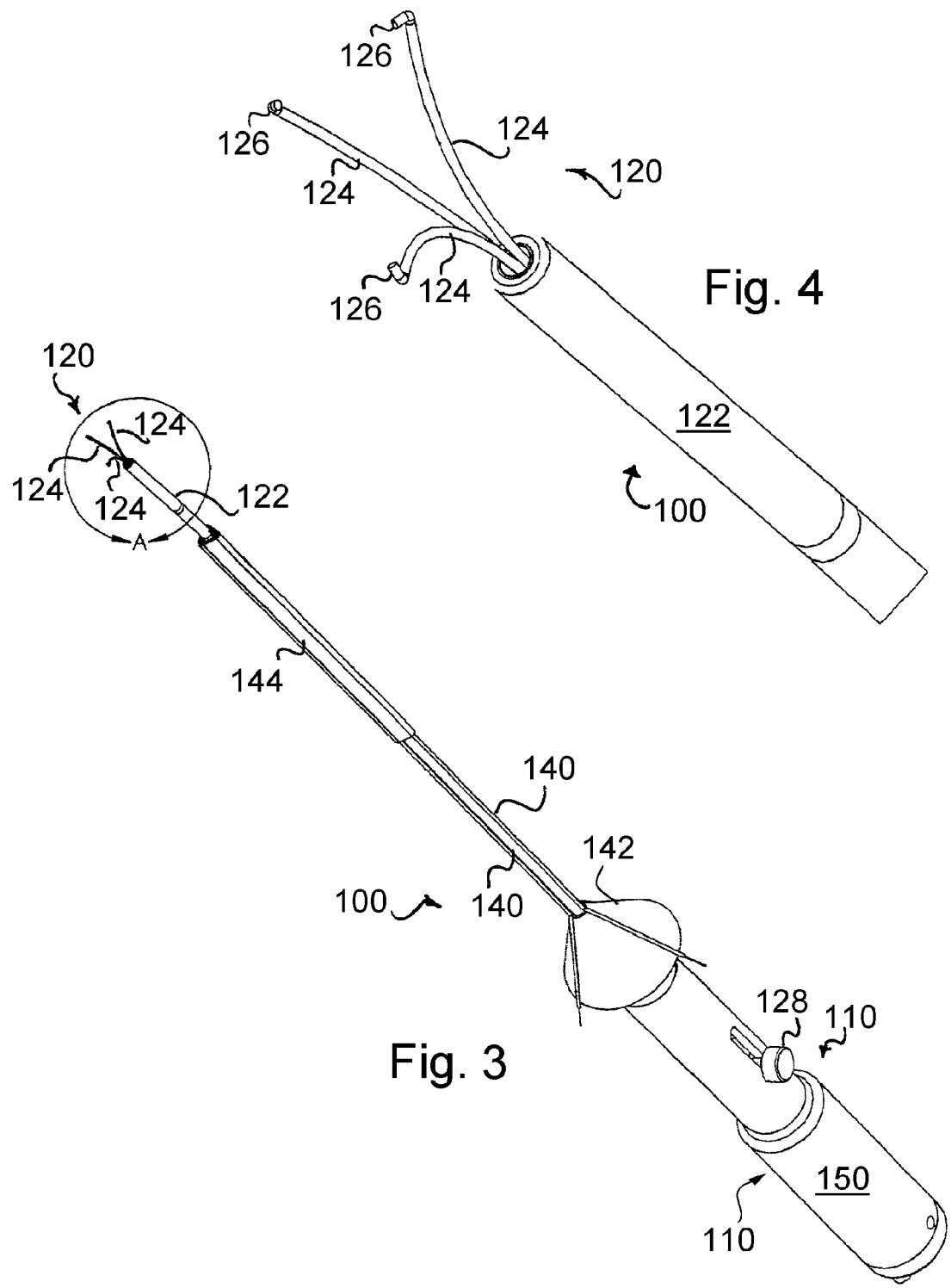

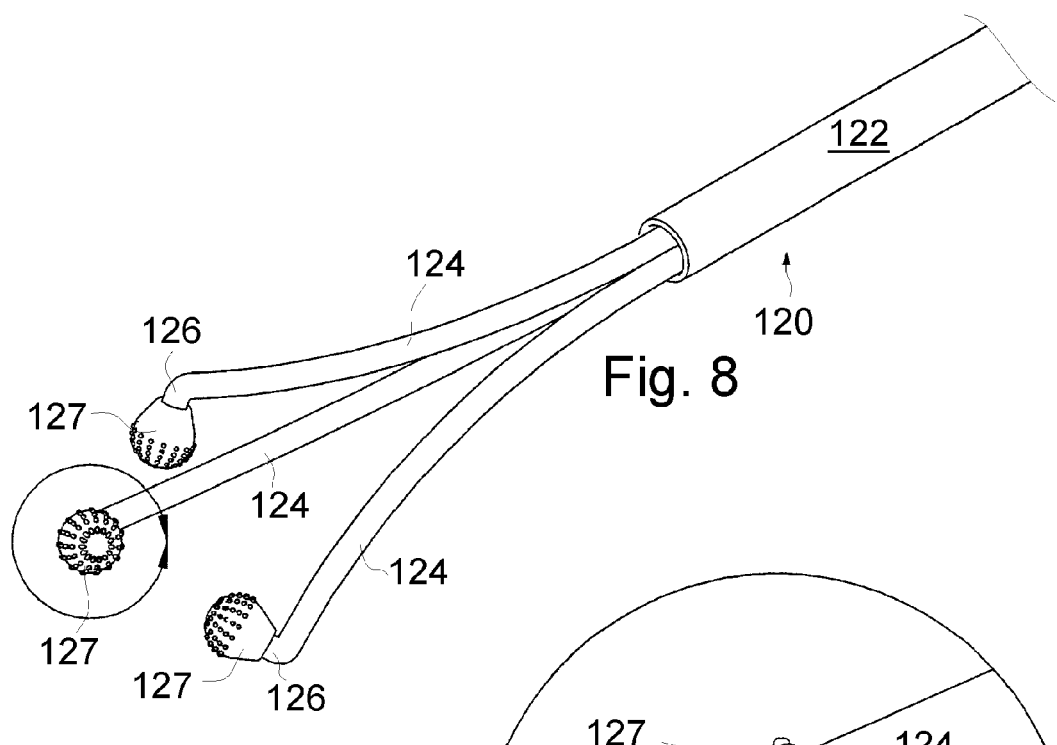
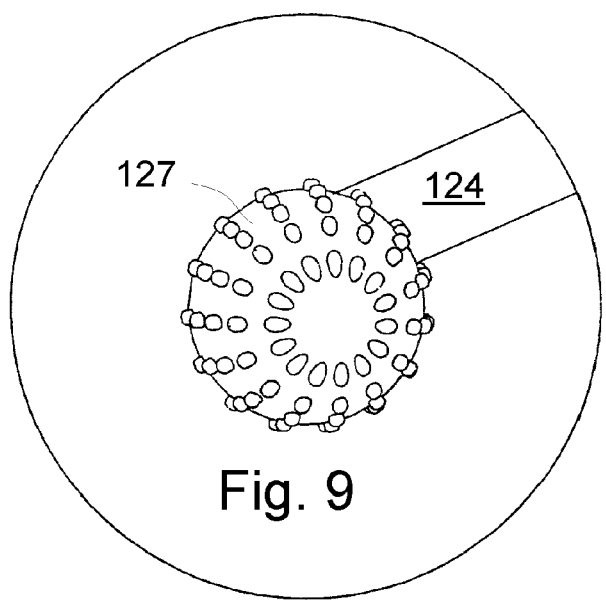

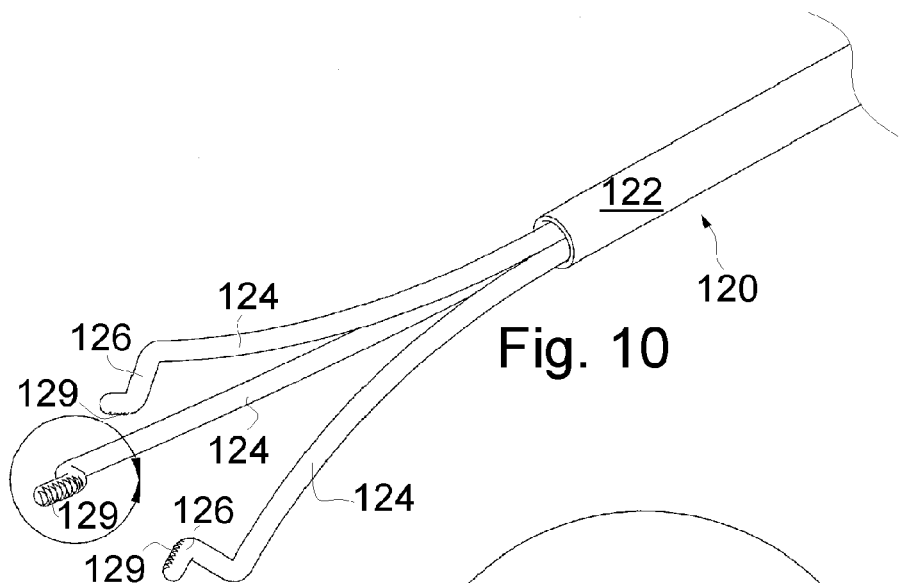
Fig. 10
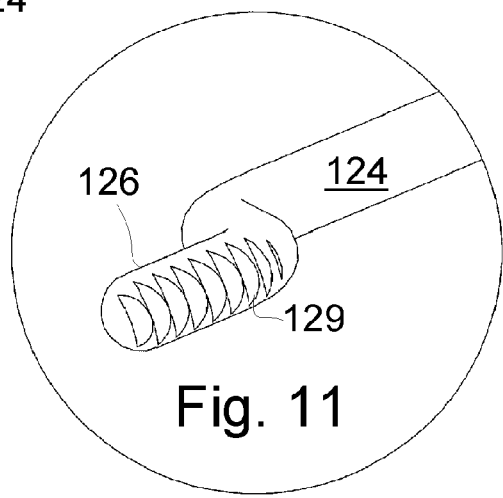
Fig. 11
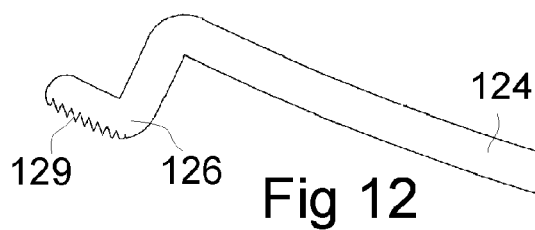
Fig 12
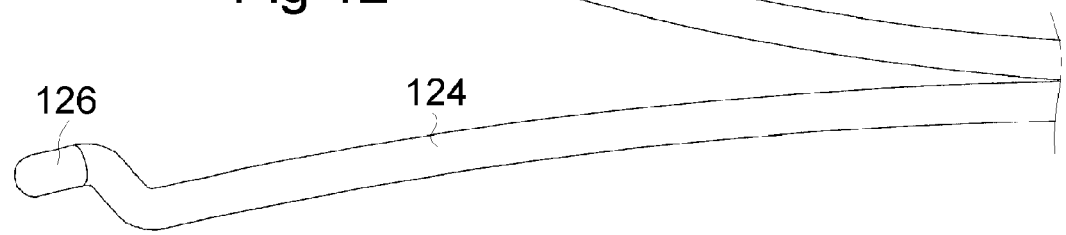

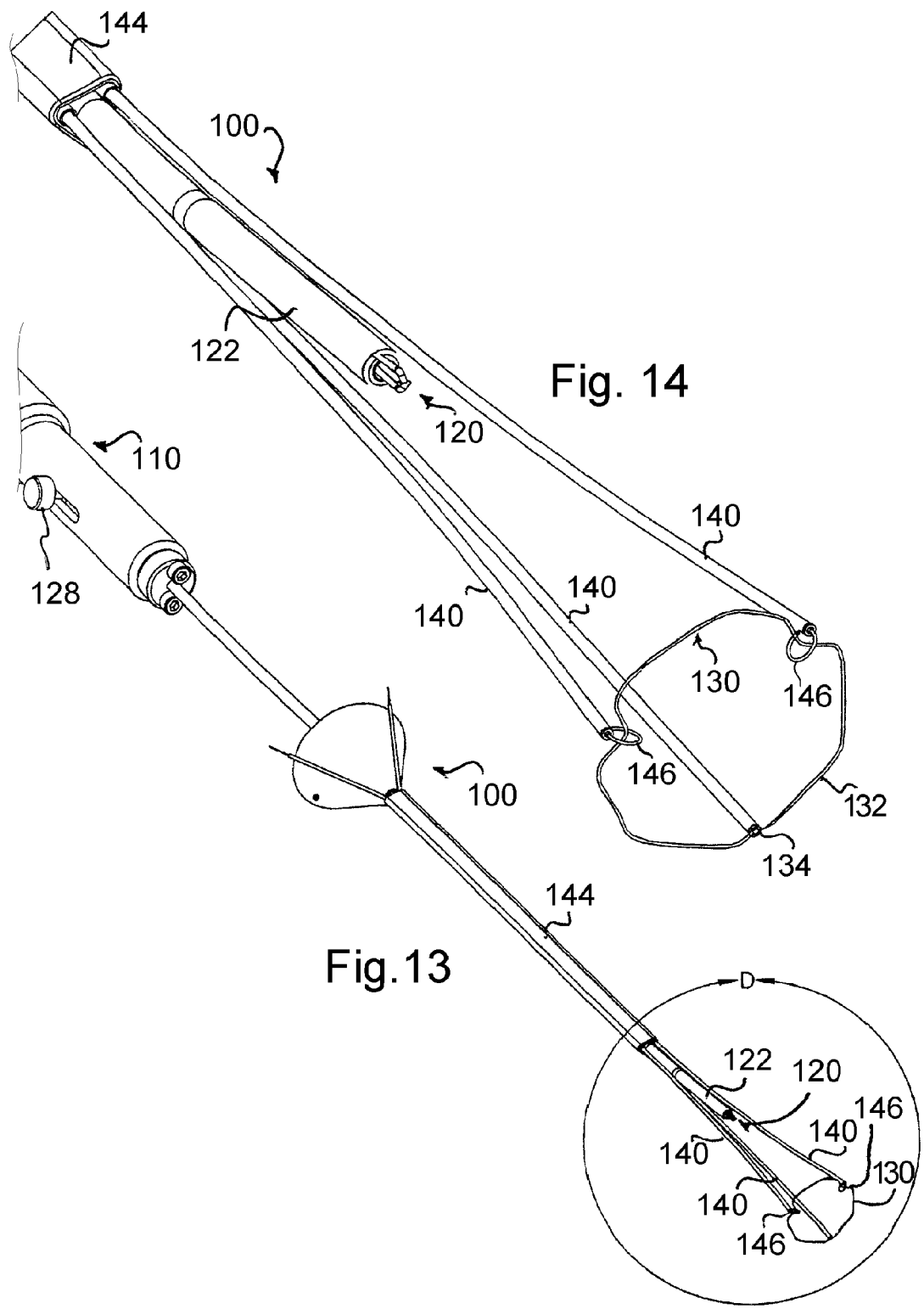

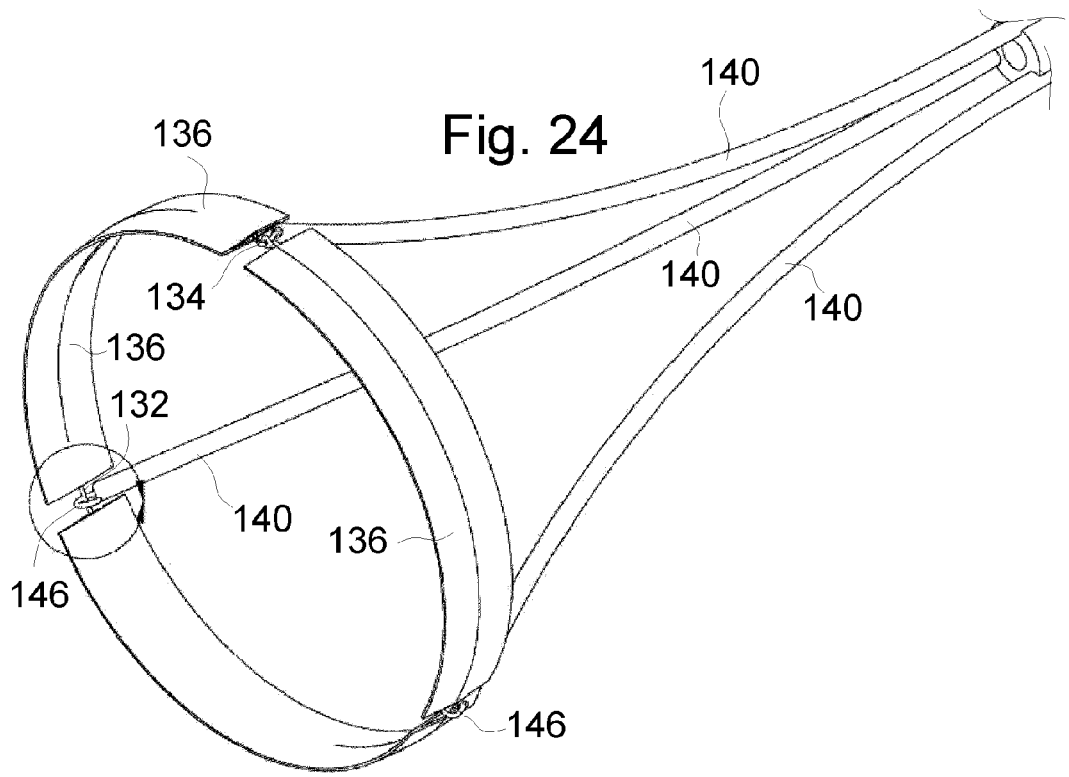
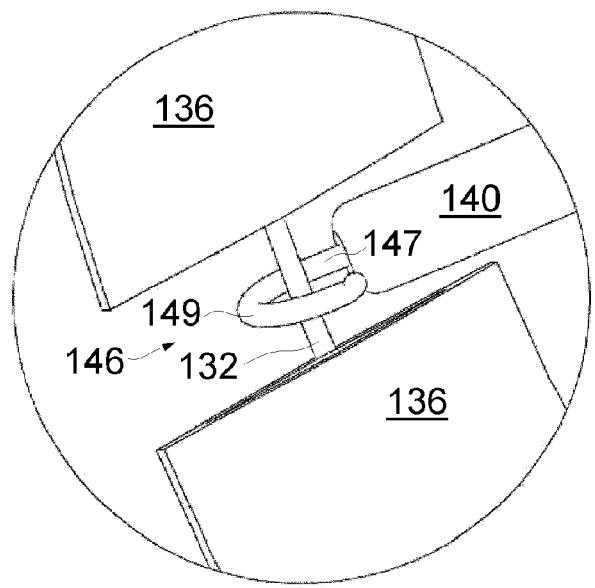

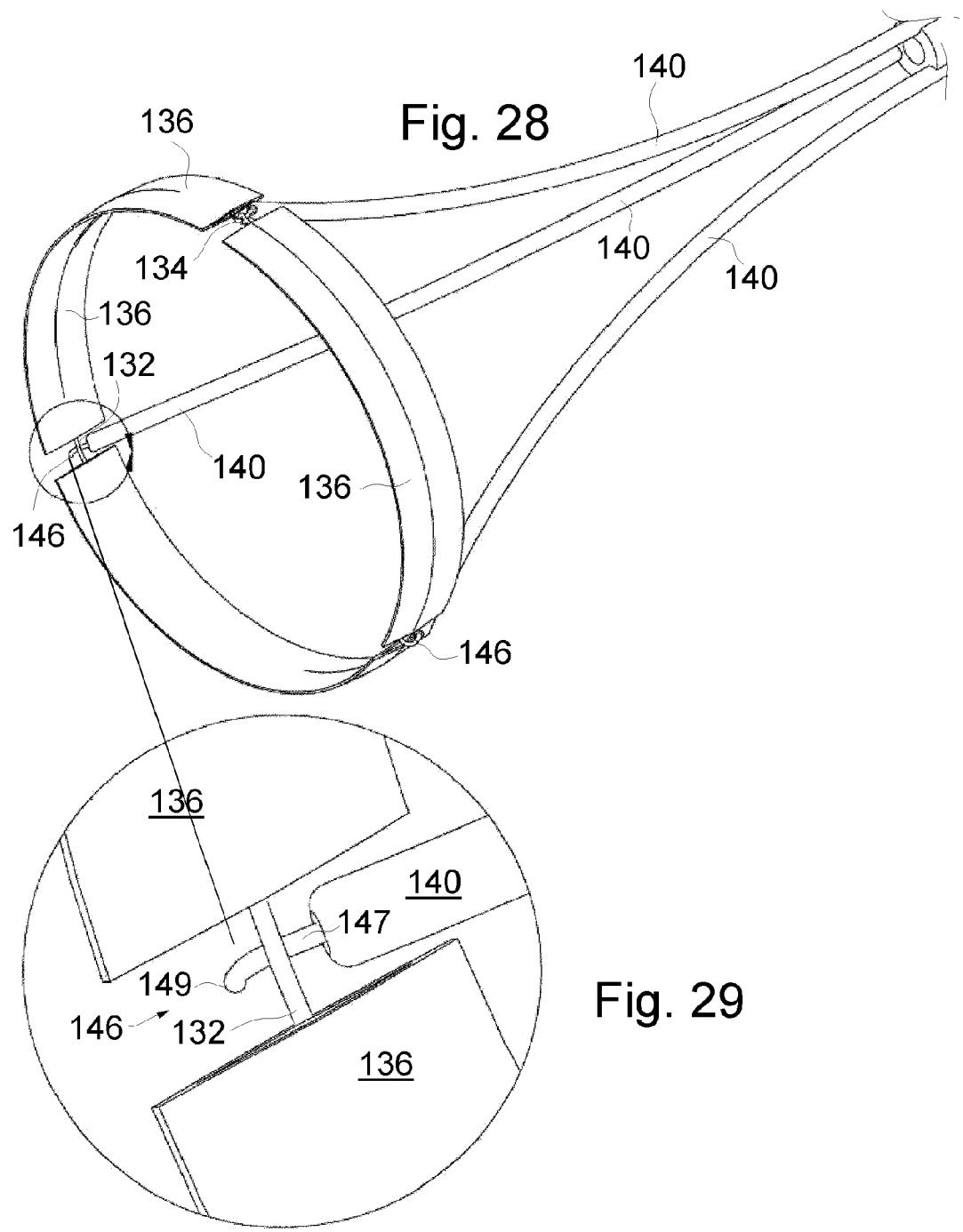

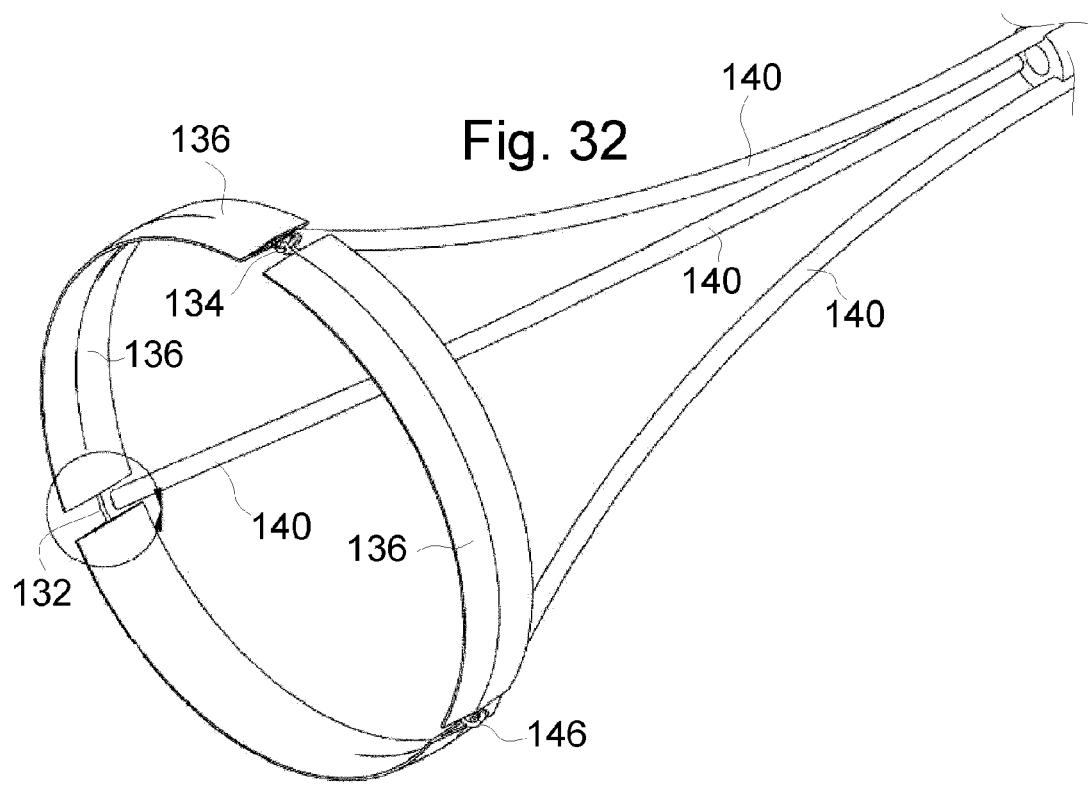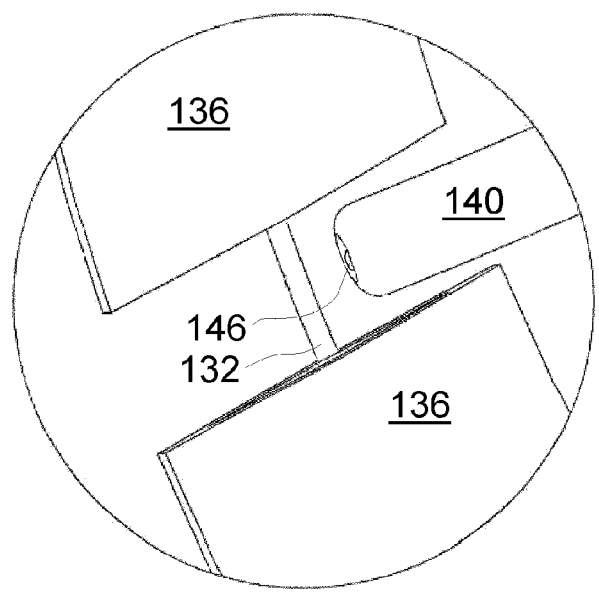

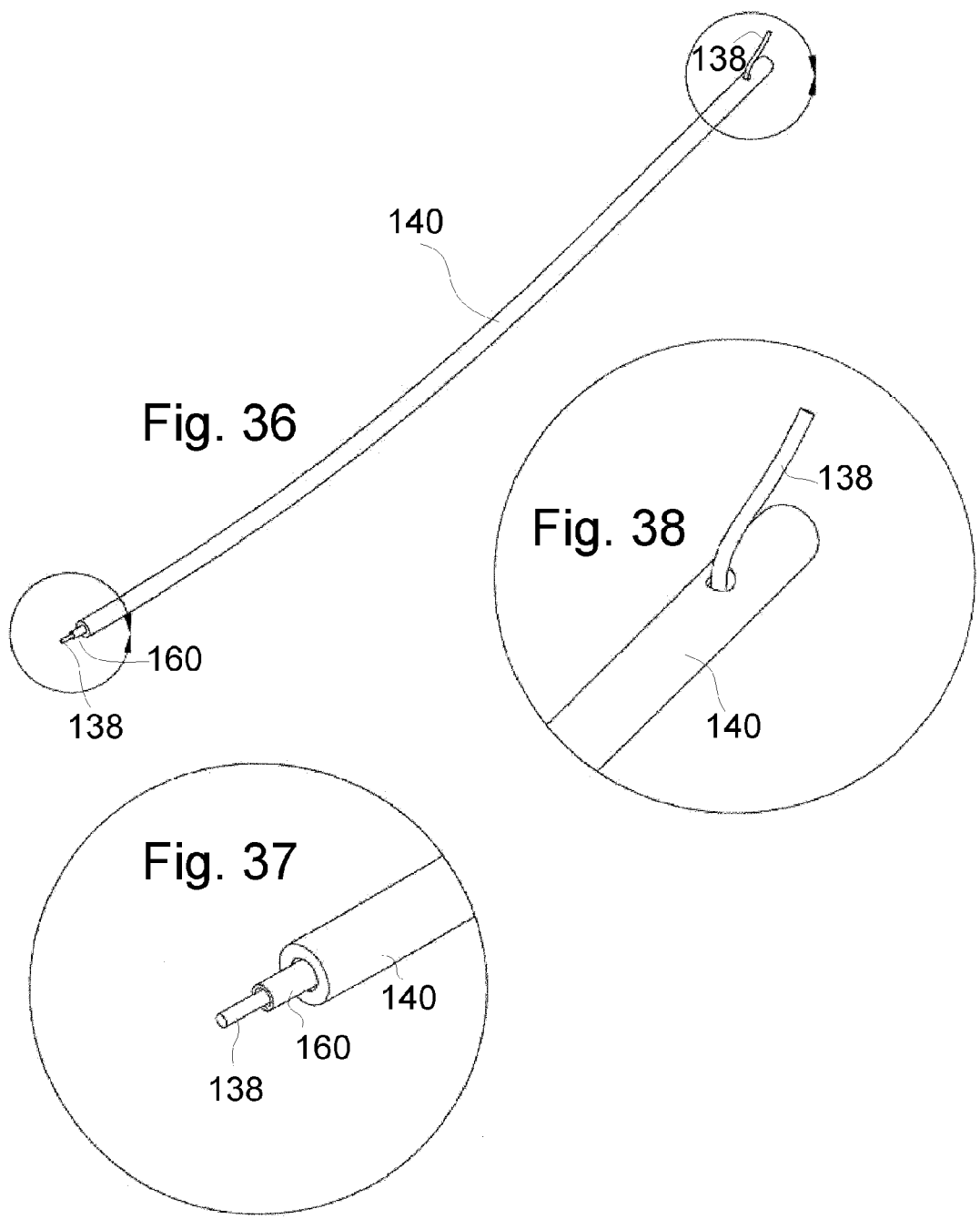

INTEGRATED MEDICAL APPARATUS FOR NON-TRAUMATIC GRASPING, MANIPULATING AND CLOSURE OF TISSUE

RELATED APPLICATIONS

This application claims the benefit of U.S. Provisional patent application Ser. No. 60/704,475 filed Aug. 1, 2005 entitled "Integrated Medical Apparatus for Non-Traumatic Grasping, Manipulating and Closure of Tissue."

BACKGROUND OF THE INVENTION

1. Field of the Invention

The present invention relates to a medical apparatus for non-traumatic grasping, manipulating and closure, and more particularly to an integrated steerable grasper and snare deploying medical apparatus for left atrial appendage isolation and closure. The invention is useful in access or approaches which do not require intercostals penetrations; however the present invention is not limited to any particular approach or access methodologies.

2. Background Information

Atrial fibrillation is a relatively common cardiac rhythm disorder affecting a population of approximately 2.5 million patients in the United States alone. Atrial fibrillation results from a number of different causes and is characterized by a rapid chaotic heart beat. During this type of fibrillation, the atria, rather than the sinus node, initiates the impulses which cause contraction of the heart muscle. In some patients, atrial fibrillation may occur in the absence of any other known disease. These impulses are relatively rapid and erratic, and are known to not properly control the contractions of the heart. As a result, the atria beat faster than the ventricles, the ventricular contractions are irregular, the ventricles do not completely fill, with blood, and the ventricular contractions eject less blood into the greater vessels.

The atrial appendages are especially important in the transport of blood because they have a sack-like geometry with a neck potentially more narrow than the pouch. In this case, contraction of the appendage is essential to maintain an average absolute blood velocity high enough to eliminate potential stasis regions which may lead to thrombus formation. One of the many problems caused by atrial fibrillation is the pooling of blood in the left atrial appendage during fibrillation. When blood pools in the atrial appendage, blood clots can accumulate therein, build upon themselves, and propagate out from the atrial appendage into the atrium. These blood clots can cause serious problems when the heart resumes proper operation (normal sinus rhythm) and the blood, along with the blood clot(s), is forced out of the left atrial appendage. Similar problems also occur when a blood clot extending from an atrial appendage into an atrium breaks off and enters the blood supply. More specifically, the blood from the left atrium and ventricle supply the heart and brain. Thus, the blood flow will move the clots into the arteries of the brain and heart which may cause an obstruction in blood flow resulting in a stroke or heart attack. Consequently, patients with atrial fibrillation also have an increased risk of stroke. It has been estimated that approximately 75,000 atrial fibrillation patients each year suffer a stroke related to that condition.

Significant efforts have been made to reduce the risk of stroke in patients suffering from atrial fibrillation. Most commonly, those patients are treated with blood thinning agents, such as warfarin, to reduce the risk of clot formation. While such treatment can significantly reduce the risk of stroke, it also increases the risk of bleeding and for that reason is inappropriate for many atrial fibrillation patients.

An alternative to the drug therapy is a procedure that closes (stitch off or remove) the left atrial appendage in patients which are prone to atrial fibrillation. Most commonly, the left atrial appendage has been closed or removed in open surgical procedures, typically where the heart has stopped and the chest opened through the sternum. Because of the significant risk and trauma of such procedures, left atrial appendage removal occurs almost exclusively when the patient's chest is opened for other procedures, such as coronary artery bypass or valve surgery.

For that reason, alternative procedures which do not require opening of the patient's chest, i.e., a large median sternotomy, have been proposed. U.S. Pat. No. 5,306,234 to Johnson describes a thoracoscopic procedure where access to the pericardial space over the heart is achieved using a pair of intercostal penetrations (i.e., penetrations between the patients ribs) to establish both visual and surgical access. While such procedures may be performed while the heart remains beating, they still require deflation of the patient's lung and that the patient be placed under full anesthesia. Furthermore, placement of a chest tube is typically required to re-inflate the lung, often requiring a hospitalization for a couple of days.

U.S. Pat. No. 5,865,791, to Whayne et al. describes a transvascular approach for closing the left atrial appendage. Access is gained via the venous system, typically through a femoral vein, a right internal jugular vein, or a subclavian vein, where a catheter is advanced in an antegrade direction to the right atrium. The intra-atrial septum is then penetrated, and the catheter passed into the left atrium. The catheter is then positioned in the vicinity of the left atrial appendage which is then fused closed, e.g., using radiofrequency energy, other electrical energy, thermal energy, surgical adhesives, or the like. Whayne et al. further describes a thoracoscopic procedure where the pericardium is penetrated through the rib cage and a lasso placed to tie off the neck of the left atrial appendage. Other fixation means described include sutures, staples, shape memory wires, biocompatible adhesives, tissue ablation, and the like. The transvascular approach suggested by Whayne et al. is advantageous in that it avoids the need to penetrate the patient's chest but suffers from the need to penetrate the intra-atrial septum, may not provide definitive closure, requires entry into the left atrial appendage which may dislodge clot and requires injury to the endocardial surface which may promote thrombus formation. A thoracoscopic approach which is also suggested by Whayne et al. suffers from the same problems as the thoracoscopic approach suggested by Johnson.

U.S. Pat. No. 6,488,689, to Kaplan et al. describes a sub-xiphoid approach for closing the left atrial appendage, and is incorporated herein by reference. The Kaplan patent discloses a tool 10 for such a closure that includes a grasper 30 and a second capture loop 32 operated by thumb guides 40 and 42 respectively. The grasper 30 and capture loop 32 extend though lumens 20, 22 or 24 in an extended body of the tool 10. The tool 10 of the Kaplan patent does not provide an efficient, convenient mechanism to actuate the grasper 30, to advance the capture loop 30, or to minimize the cutting effects of the capture loop 30. The Kaplan et al. patent further describes a clip applying surgical device that suffers from similar difficulties.

There is a need for a surgically acceptable tool for minimally invasive left atrial appendage closure. Such a tool would be capable of being used on patients who have received only a local anesthetic and whose hearts have not been stopped. It would be further desirable to provide an effective, efficient, easily utilized surgical tool that allows for procedures which approach the left atrial appendage without the need to perform a thoracotomy (i.e. penetration through the intercostal space) or the need to perform a transeptal penetration and/or perform the procedure within the left atrium or left atrial appendage. At least some of these objectives will be met by the inventions described herein below.

It is the objects of the present invention to address the deficiencies of the prior art discussed above and to do so in an efficient cost effective manner

SUMMARY OF THE INVENTION

It is noted that, as used in this specification and the appended claims, the singular forms "a," "an," and "the" include plural referents unless expressly and unequivocally limited to one referent. For the purposes of this specification, unless otherwise indicated, all numbers expressing any parameters used in the specification and claims are to be understood as being modified in all instances by the term "about." All numerical ranges herein include all numerical values and ranges of all numerical values within the recited numerical ranges.

The various embodiments and examples of the present invention as presented herein are understood to be illustrative of the present invention and not restrictive thereof and are non-limiting with respect to the scope of the invention.

At least some of the above stated objects are achieved with the minimally invasive medical tool for the non-traumatic grasping, manipulation and closure of tissue such as a tool for left atrial appendage closure according to the present invention. The present invention includes an operator handle end and a multi-prong grasping member positioned within and movable relative to a grasper lumen that extends from the handle end, wherein the grasping prongs are moved between an open and closed position by relative axial movement between the prongs of the grasping member and the grasper lumen. The invention includes a contractible snare and a plurality of axially moveable snare pushing arms. At least two of the snare pushing arms include a snare holding and release mechanism, wherein the snare pushing arms are configured to advance the snare in an open, encircling position to a final deployed position where the snare can be released through the activation of the holding and release mechanism of the pushing arms, and finally tightened in a conventional fashion, such as pulling on an end of the snare at the handle end.

These and other advantages of the present invention will be clarified in the brief description of the preferred embodiment taken together with the drawings in which like reference numerals represent like elements throughout.

BRIEF DESCRIPTION OF THE DRAWINGS

FIG. 1 is a perspective view of an integrated possibly steer-able grasper and snare deploying medical apparatus for left atrial appendage isolation according to the present invention with the grasping member in a withdrawn and closed position and the snare omitted for clarity;

FIG. 2 is an enlarged view of the grasping member of the medical apparatus of FIG. 1;

FIG. 3 is a perspective view of the integrated steer-able grasper and snare deploying medical apparatus of FIG. 1 with the grasping member in an advanced and open position and the snare omitted for clarity;

FIG. 4 is an enlarged view of the grasping member of the medical apparatus of FIG. 3;

FIG. 8 is an enlarged view of another modified grasping member of the medical apparatus of FIG. 3;

FIG. 9 is a further enlarged view of a single grasping element of the modified grasping member of FIG. 8;

FIG. 10 is an enlarged view of another modified grasping member of the medical apparatus of FIG. 3;

FIG. 11 is a further enlarged view of a single grasping element of the modified grasping member of FIG. 10;

FIG. 12 is an enlarged view of a pair of grasping elements of the modified grasping member of FIG. 10;

FIG. 13 is a perspective view of the integrated steer-able grasper and snare deploying medical apparatus of FIG. 1 with the grasping member in an retracted and closed position and a snare in an advancing and open position;

FIG. 14 is an enlarged view of the snare, the snare pushing arms and the holding and release mechanism of the snare holding arms of the medical apparatus of FIG. 13;

FIGS. 16-33 are alternating perspective and enlarged perspective views of a modified snare and the snare release mechanism in sequential operation through the snare release position;

FIG. 36 is a perspective view of a modified snare pushing arm with a snare contracting lead there through and a snare trimming member;

FIG. 37 is an enlarged view of the operator's end of the snare pushing arm of FIG. 36;

FIG. 38 is an enlarged view of the distal end of the snare pushing arm of FIG. 36;

FIG. 43 is an enlarged view of the operator handle end of the apparatus illustrating the steering control for the apparatus; and.

DESCRIPTION OF THE PREFERRED EMBODIMENTS

Figure 5:
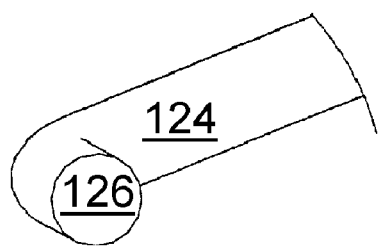
FIG. 5 is a further enlarged view of a single grasping element of the grasping member of FIG. 3.

A steer-able, minimally invasive medical apparatus or tool 100 for left atrial appendage closure according to the present invention is generally illustrated in FIGS. 1-9. The tool 100 may be referred to as a surgical device but need not be limited to a surgical apparatus. Consequently, within the meaning of this application the term "surgical" will broadly reference any medical application. The present invention includes an operator handle end 110 with controls, to be described herein after, positioned at one axial end of the apparatus 100. The term "axial" within the meaning of this specification will reference extending along the length of the apparatus 100. In some embodiments of the present invention the apparatus 100 may extend along a curve rather than in one straight direction. Further, as will be described below, the apparatus 100 may be steered to curve the leading distal end of the apparatus 100.

A multi-prong grasping member 120 is positioned within and movable relative to a grasper lumen 122 that extends from the handle end 110. FIGS. 1 and 2 are perspective views of the surgical apparatus 100 with the grasping member 120 in a withdrawn and closed position {and a snare thereof, described below, omitted for clarity}. FIGS. 3 and 4 are perspective views of the surgical apparatus 100 with the grasping member 120 in an advanced and open position and the snare omitted for clarity.

The grasping elements or prongs 124 may be formed as a plurality of wires with gripping ends 126 designed to maximize the gripping of the left atrial appendage tissue. The prongs 124 preferably have a memory such that they move to the open position as they extend from the grasper lumen 122, whereby the axial movement of the prongs 124 relative to the grasper lumen 122 will open and close the grasping member 120. The prongs 120 may be formed of a polymer based material, but metal wires have the needed memory and are readily available. Nitinol wires or wires from a spring steel alloy are also believed to be suitable, available and effective.

Figure 6:
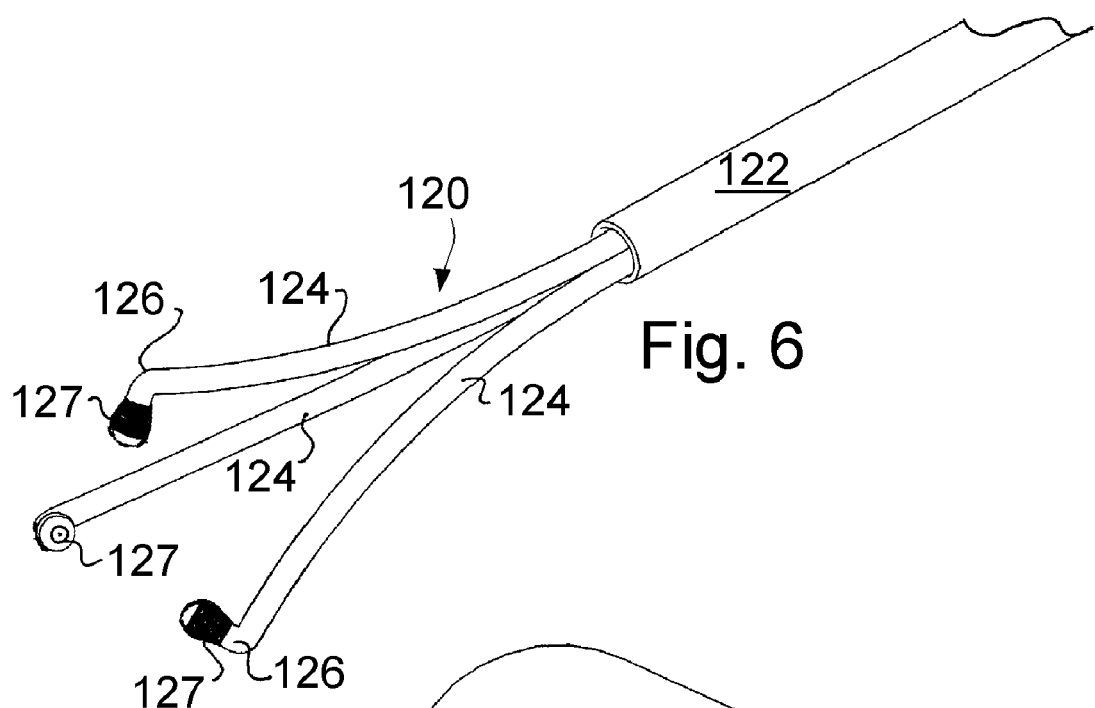
FIG. 6 is an enlarged view of a modified grasping member of the medical apparatus of FIG. 3.
Figure 7:
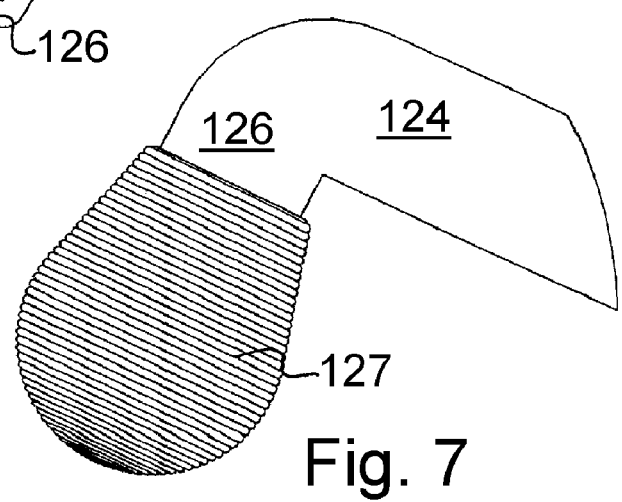
FIG. 7 is a further enlarged view of a single grasping element of the modified grasping member of FIG. 6.

The gripping ends 126 of the prongs 124 may take any number of forms that maximize tissue gripping function and minimize tissue damage. FIGS. 3-5 illustrate gripping ends 126 formed of bare wire bent to be perpendicular to the prongs 124 as shown. The bare wire may be more traumatic to the tissue than other possible designs. The gripping ends 126 may be formed as a protective, high friction, textured or "sticky" cover 127 over the ends 126 of the wires forming the prongs 124, as shown in FIGS. 6-9. Specifically FIGS. 6-7 illustrate the cover 127 formed by wrapping the ends 126 with suture material. The suture material forming the cover 127 protects the tissue from the ends 126 of the prong 124 (bare wire) and increases the friction for the gripping action. FIGS. 8-9 illustrate textured rubber caps forming the covers 127. The covers 127 could be formed of foam, rubber, or polymer. The covers could be formed by dipping the ends 126 in a UV-curable medical glue. Alternatively, as shown in FIGS. 10-12 the ends 126 can include serrations or ridges 129. As noted above, in each embodiment, the grasping prongs 124 are moved between an open and closed position by relative axial movement between the prongs 124 of the grasping member 120 and the grasper lumen 122.

Three prongs 124 are shown and generally preferred, but any desired plurality of prongs 124 can be used in a similar fashion. The memory in the material forming the prongs 124 will move the prongs 124 to the open position as the prongs 124 exit the end of the grasper lumen 122. A control knob, trigger or slide 128 on the handle end 110 allows the operator to easily actuate the grasping member 120 and move the grasping prongs 124 between the open and closed position as best illustrated in the figures. Preferably the slide 128 of the grasping member 120 is spring biased to the closed position shown in FIGS. 1 and 2 whereby once the tissue is captured by the grasping member 120 the spring bias will maintain a hold on the tissue so the user can continue with the procedure without actively holding the tissue. The slide 128 of the grasping member 120 can be advanced at the end of the procedure to release the tissue. It is also contemplated that the handle end 110 of the apparatus 100 will take the shape of a pistol-grip, and that slide 128 will be a finger actuated trigger for the convenience and comfort of the operator.

Figure 15:
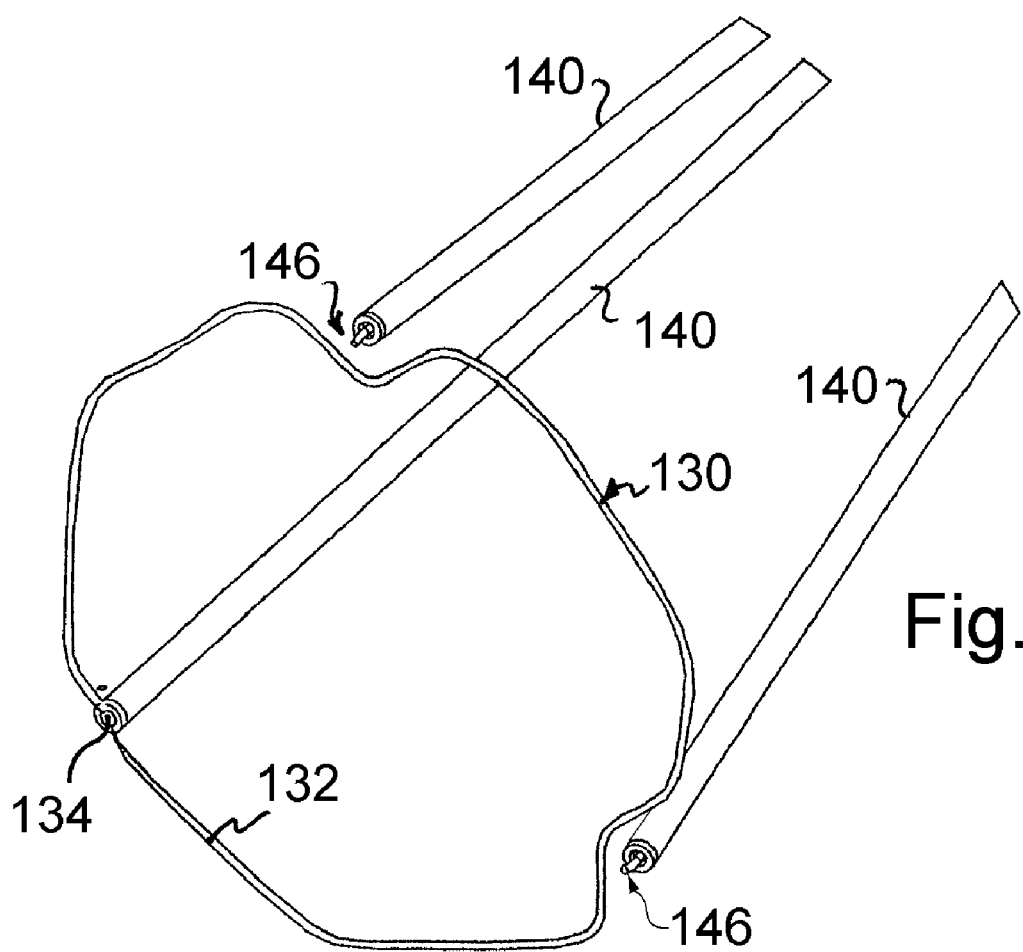
FIG. 15 is an enlarged view of the snare, the snare pushing arms and the holding and release mechanism of the snare holding arms of the medical apparatus of FIG. 13, with the holding and release mechanism of the pushing arms in the release position for snare deployment.
Figure 16:
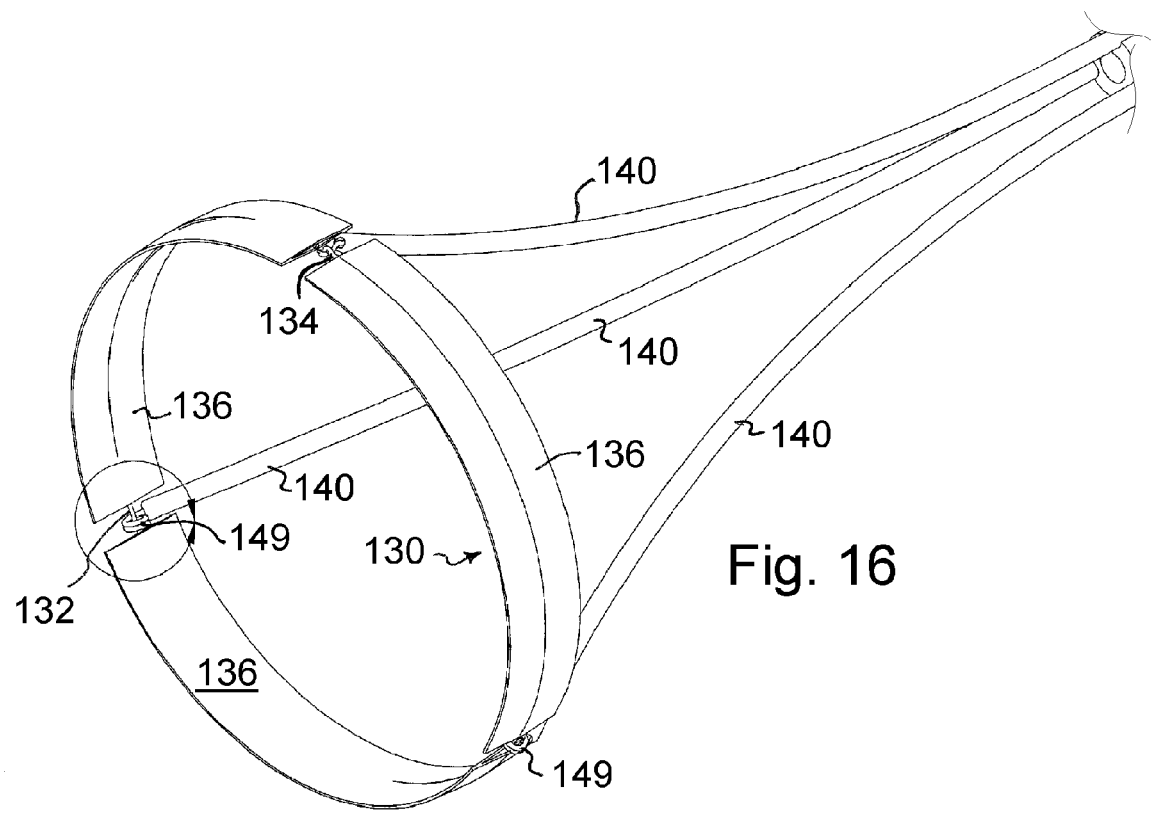
Figure 17:
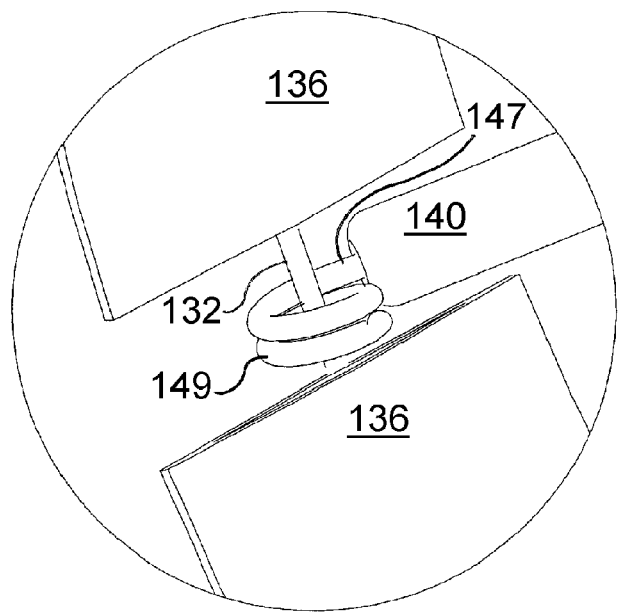
Figure 18:
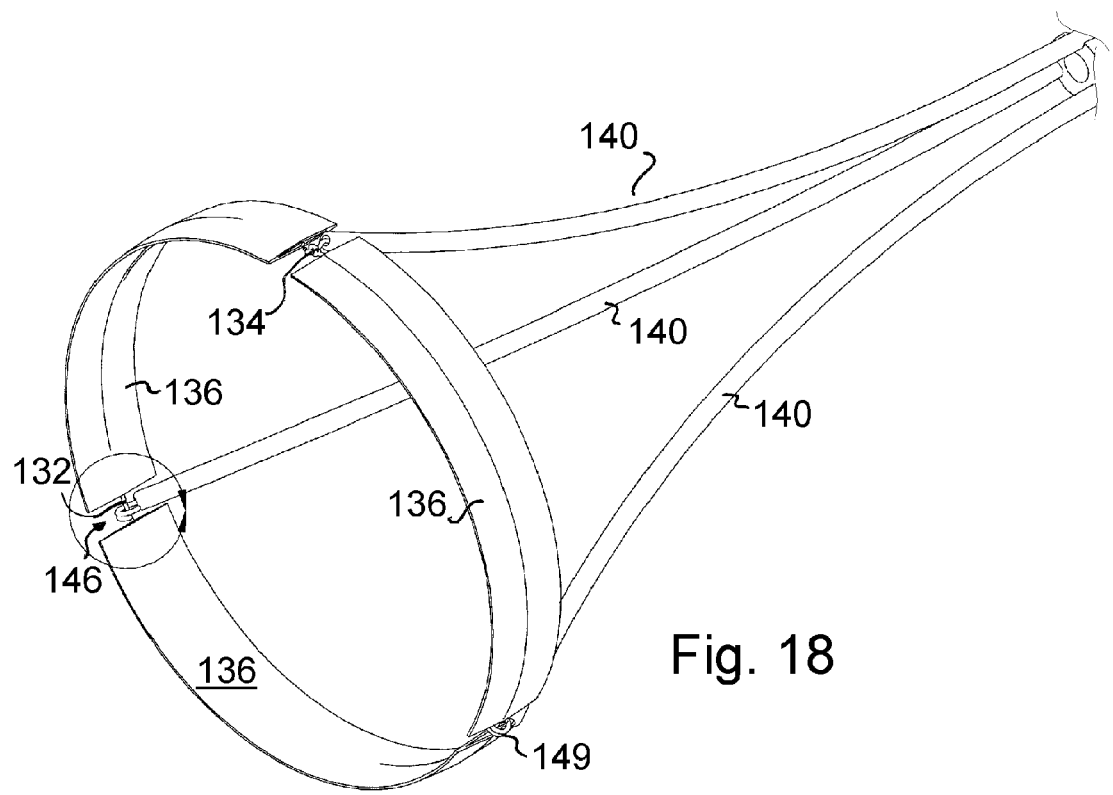
Figure 19:
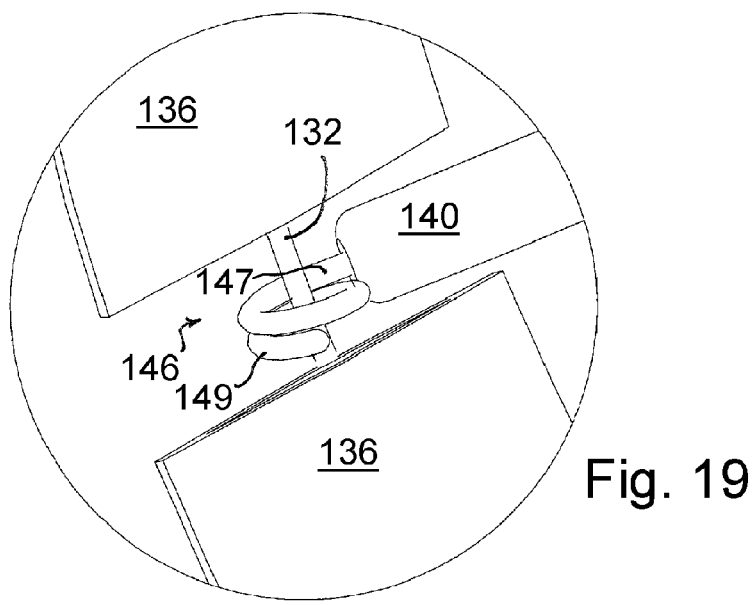
Figure 20:
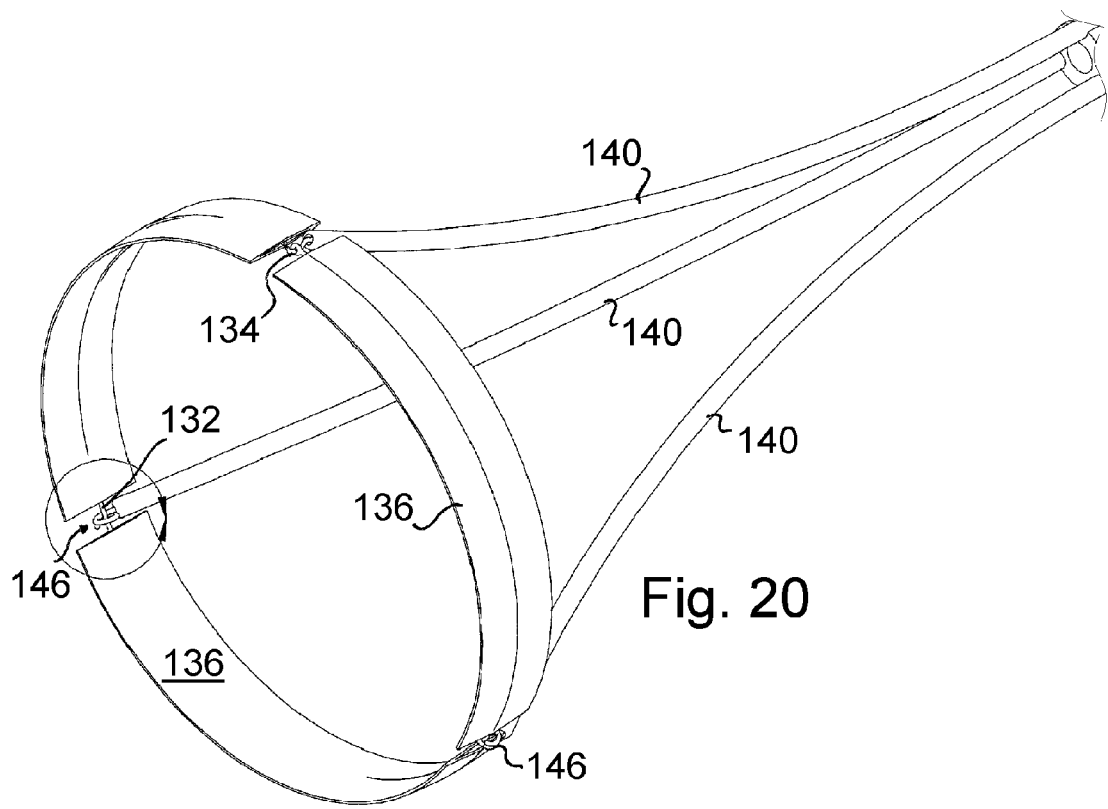
Figure 21:
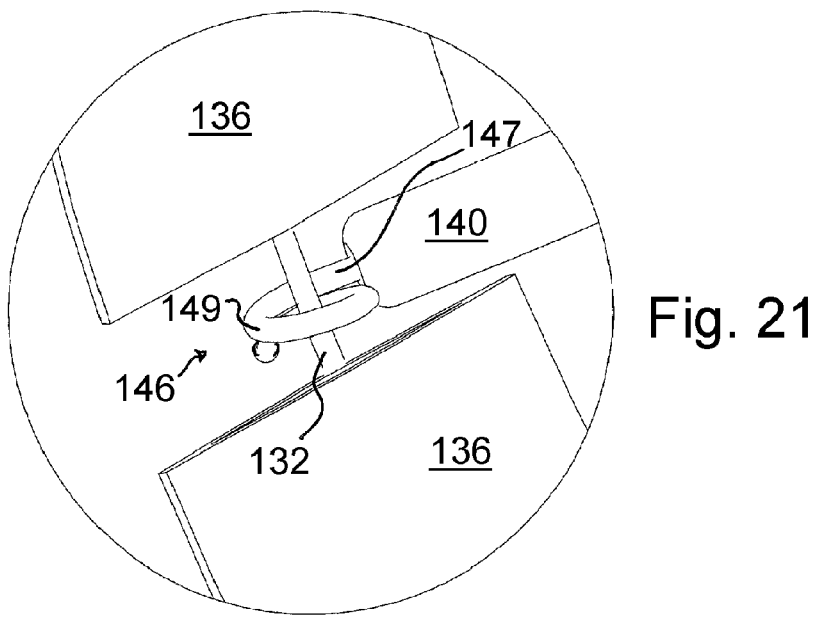
Figure 22:
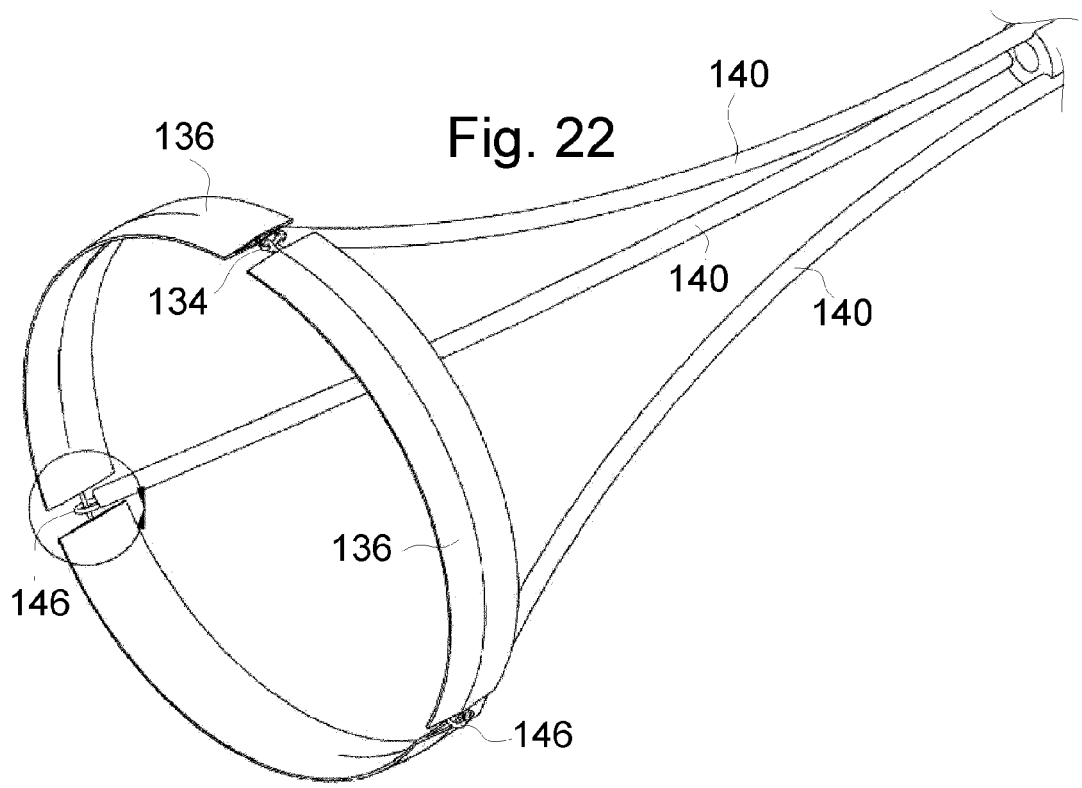
Figure 23:
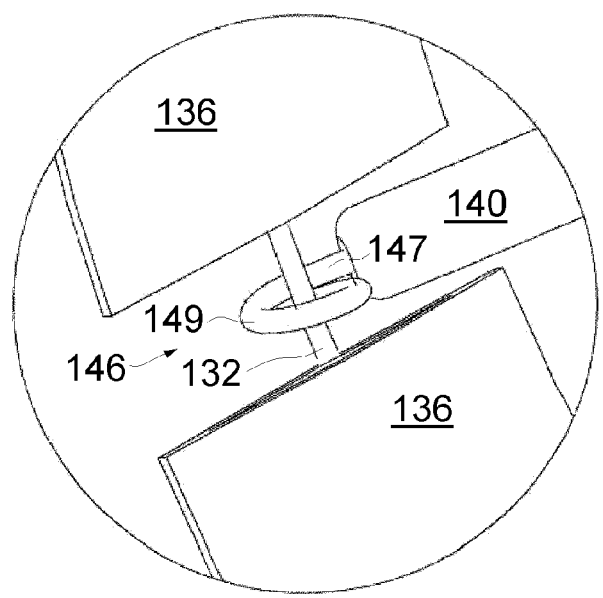
Figure 26:
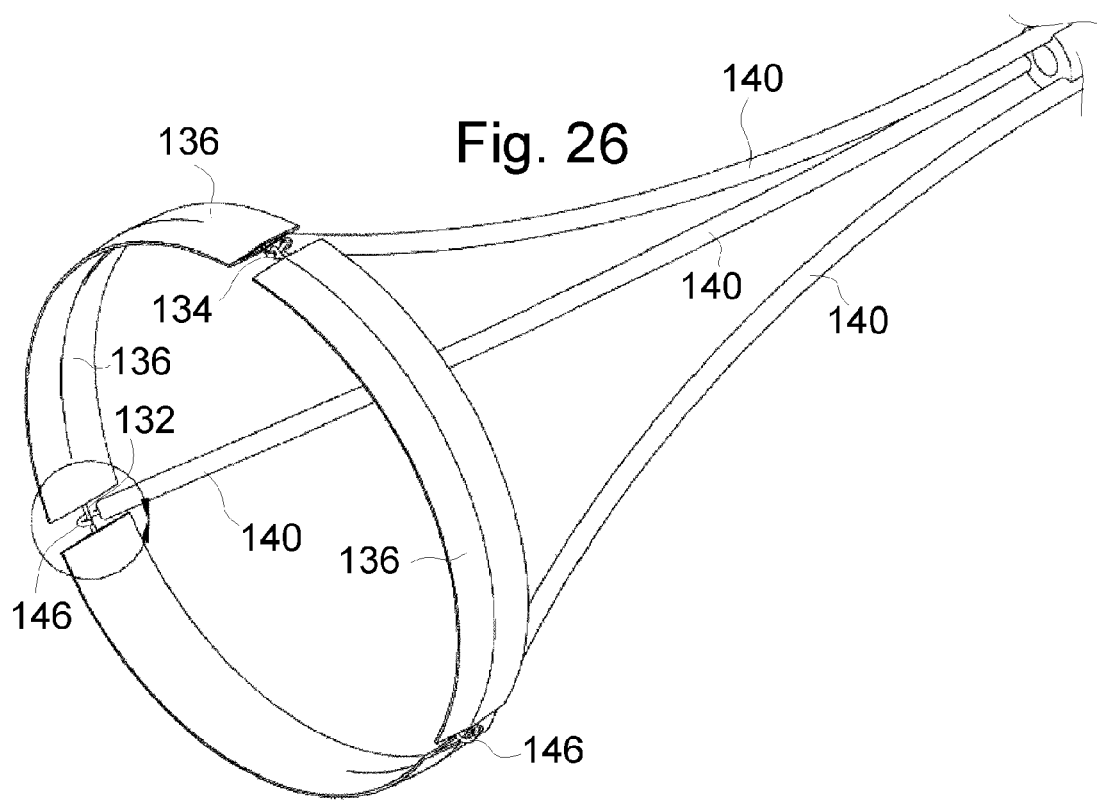
Figure 27:
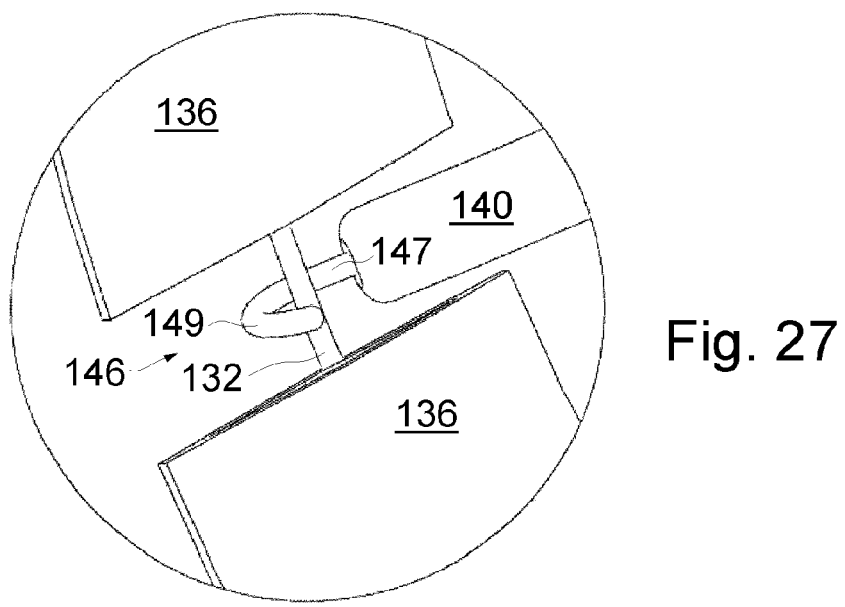
Figure 30:
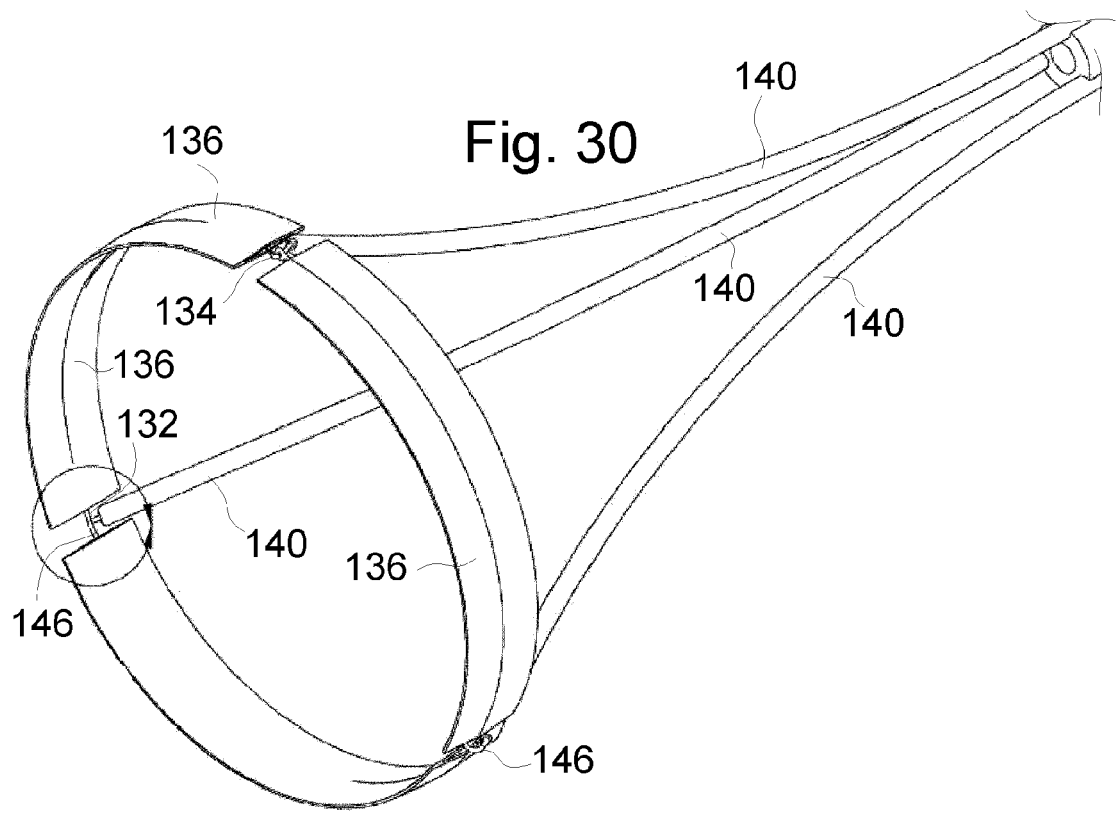
Figure 31:
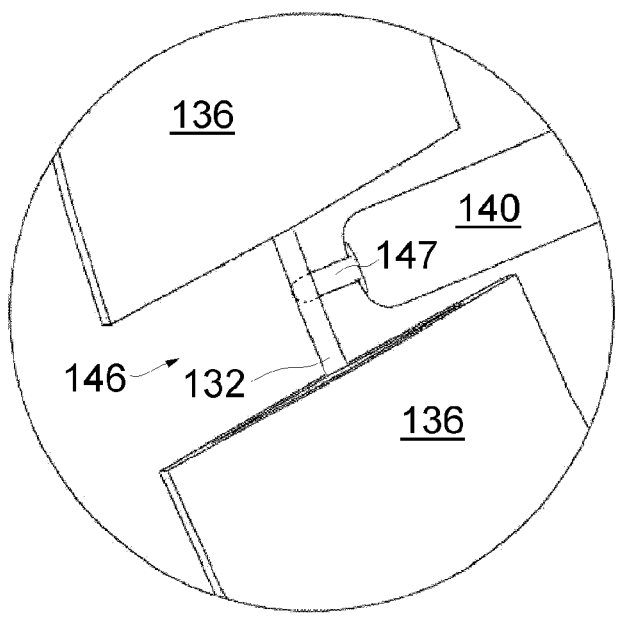
Figure 34:
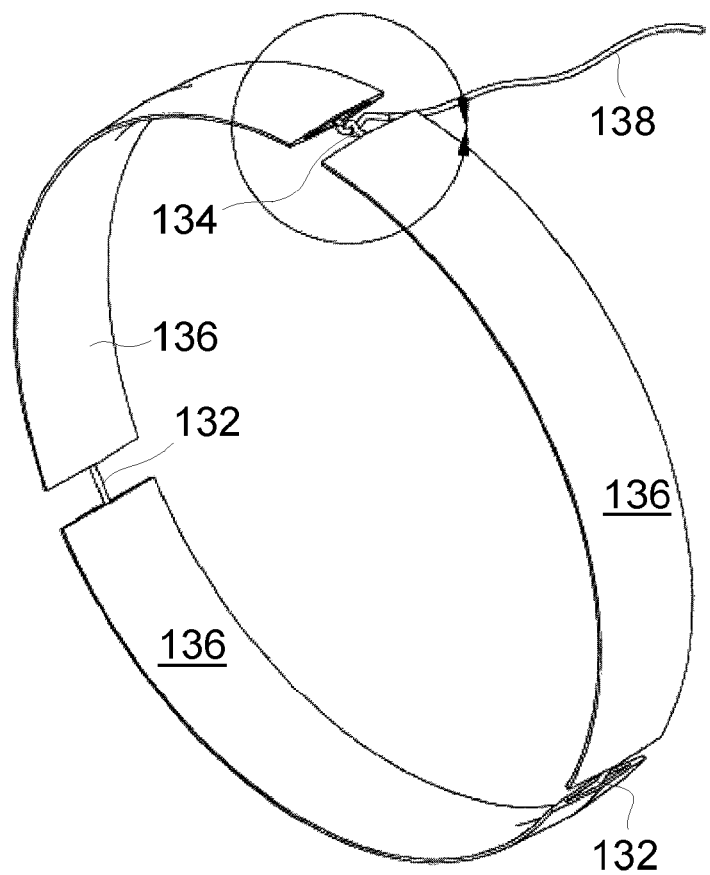
FIGS. 34-35 are alternating perspective and enlarged perspective views of the modified snare and snare tightening mechanism of FIG. 16.
Figure 35:
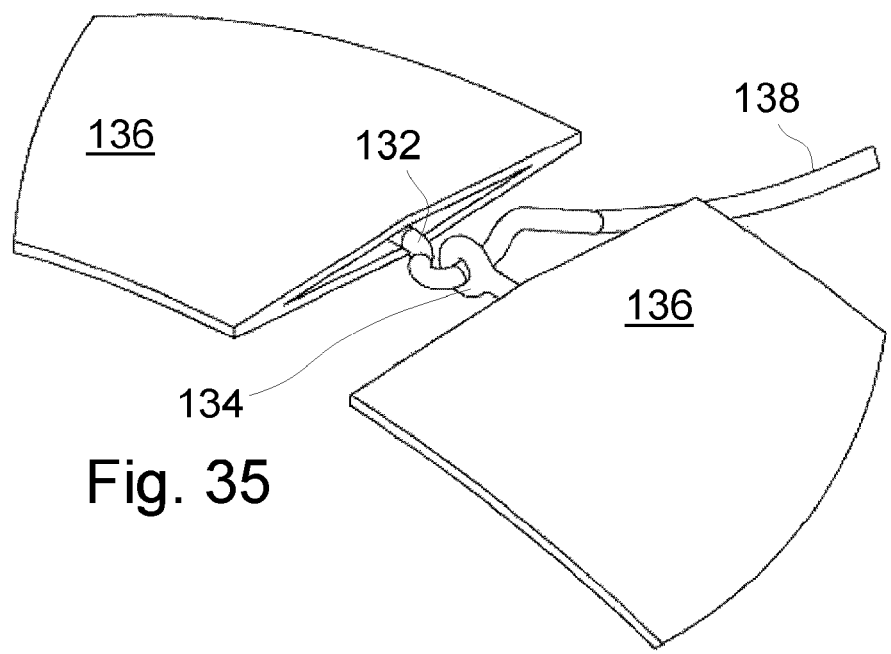
Figure 39:
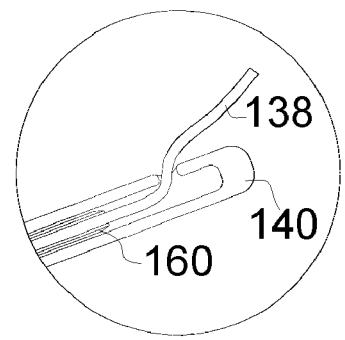
FIGS. 39-41 are enlarged section views of the distal end of the snare pushing arm of FIG. 36 illustrating, sequentially the trimming operation.
Figure 40:
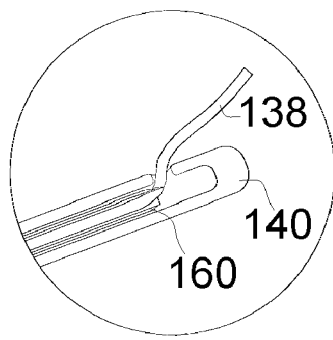
Figure 41:
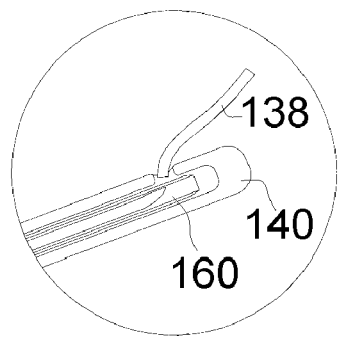

The apparatus 100 includes a contractible snare 130, shown in FIGS. 13-15, which may be formed in a conventional fashion. Specifically the snare 130 may be a looped flexible material 132 such as a wire or suture material having a slip-knot, or a crimped metal member, a push knot locking member, a ratchet wire tie stop (operable for repositioning, or other slip lock feature 134 allowing the snare 130 to be tightened and held in the desired position following tightening, and a control end extending to the distal handle end 110 of the apparatus 100. The operation and construction of snares 130, in general, is well known in the art.

FIGS. 16-35 illustrate a modified snare 130 in accordance with one aspect of the present invention in which the snare 130 is formed as a loop of flexible material 132 such as a suture material fiber polymer (e.g. nylon) or a metal wire. A further modification is to form the material 132 from a wire that is barbed in one direction only to further hold the snare 130 in the deployed and closed position. However, tests with suture material and slip knots alone have found the snares 130 so formed will maintain the closed position around the left atrial appendage to a sufficient degree.

The modified snare 130 further includes a textured band of material around the wire or material 132 at the looped end in the form of a series of sheaths 136 for the purposes of distributing the forces of the snare 130 as it is tightened and deployed around the left atrial appendage. The purpose of the snare 130 is to close the left atrial appendage as opposed to cutting into or cutting off this appendage, so a band of material, such as sheaths 36, around the operating loop of the wire of the snare 130 will help avoid any unwanted cutting of the tissue. The sheaths 136 may be formed from reinforced polypropylene mesh material to provide a non-traumatic, non-tearing, non-abrasive surface against the tissue. It is contemplated that only the inside (side facing the tissue) of the sheaths 136 is textured to increase the friction between the snare 130 and the tissue to further maintain the deployed snare 130 around the tissue. Maintaining the outside of the sheaths 136 as smooth, or un-textured, may be beneficial in preventing unwanted interference or abrasion with the outside of the deployed snare 130.

The sheaths 136 could be formed from polypropylene on one side and PTFE material on the other to provide the desired dual properties. The sheaths 136 could also be a single sheath around the wire member 132, but the separate sheaths 136 allow for easily accommodating the holding and release mechanism (described below), the slip lock member 134 (shown in detail in FIGS. 35-36), and the lead or control end 138 of the flexible member 132, and allows for the cinching of the snare 130 without an over bunching of the sheaths 136. The snare 130 construction allows the operator to close a major cavity of the left atrial appendage without restricting the micro-vascular structure of the left atrial appendage to avoid tissue necrosis. In other words, the snare 130 will close the left atrial appendage cavity without cutting off the blood supply to the tissue forming the appendage.

The apparatus 100 includes a plurality of axially moveable snare pushing arms 140 that are axially moveable relative to the grasper lumen 122. The pushing arms 140 extend along the apparatus 100 to the handle end and are attached to an axially moving snare deployment knob or control 142. Axial movement of the control 142 will axially move the snare pusher arms 140 and the associated snare 130, until deployed. An axially sliding pushing arm containment sleeve 144 is provided to hold the pusher arms 140 in a retracted position for insertion of the apparatus 100. After the left atrial appendage has been grasped by the grasping member 120, the containment sleeve 144 can be slid back toward the deployment control 142 to open the snare 130 and to open the pusher arms 140 for snare deployment.

As best illustrated in FIGS. 16-33 at least two of the snare pushing arms 140 include a snare holding and release mechanism 146. FIGS. 13 and 14 are perspective views of the surgical apparatus 100 of FIG. 1 with the grasping member 120 in a retracted and closed position and the snare 130 in an advancing and open position. Specifically the pushing arms 140 may be formed as lumens with the snare holding and release mechanism 146 of each pushing arm 140 formed as a wire 147 extending through the lumen forming the pushing arm 140 and a wire loop 149 at the end of the lumen. The wire 147 extends through the lumen to the deployment control 142. When the operator desires to release the snare 130 from the pushing arms 140, the wires 147 forming the holding and release mechanism 146 are pulled through the lumens forming the pushing arms 140. The operator has access to the other end of the wires forming the holding and release mechanism at the deployment control 142. As the wire 147 forming the snare holding and release mechanism 146 are pulled through the lumen forming the pushing arms 140 the holding loop 147 at the end will uncoil thereby releasing the snare 130 for deployment as shown in FIG. 7.

FIGS. 16-33 are alternating perspective and enlarged perspective views of a modified snare 130 and the snare release mechanism 146 formed of wire 147 and coil wire loop 149 in sequential operation through the snare release position. The wires 147 have a memory such that the coil wire loop 149 is formed as the wires 147 exit the lumen of the arms 140, and the wires 147 are flexible enough to be withdrawn through the lumen whereby the axial movement of the wire 147 relative to the lumen forming the arm 140 will open and close (coil and un coil) the loop 149. It should be apparent to those of ordinary skill in the art that the snare release mechanism forms a simple, flexible grasping member, such as for grabbing lead wires remotely, or the like. The wire 147 and loop 149 may be formed of a polymer based material, if it had the sufficient memory. Consequently the term "wire" is not intended to be limited to a particular material, rather merely defining the elongated shape of the subject material. For example, the wire 147 could be formed as a rectangular sheet material that has sufficient memory to form a loop. Spring alloy steels may also be suitable. Nitinol wire has been found to exhibit the needed memory and is readily available. Although the pushing arm 140 and release mechanism 146 are disclosed for deployment and releasing in this embodiment, other devices could easily use this structure for grasping as discussed above. The present invention, as shown, provides for multiple coils or loops forming loop 149 in the non-release or grasping position, however only a single loop would be required for effective grasping. Within the meaning of this application a curvature of about 180° would be sufficient to form a "loop", and an effective grasper could be formed with only a single 180° turn in the wire 147 forming a single "loop". A closed loop of at least 360° for the wire 147 is believed to be more secure, and multiple coils as shown in loop 149 provide even more security particularly when used to advance or retract a grasped item.

The snare pushing arms 140 are configured to advance the snare 130 in an open, encircling position to a final deployed position where the snare 130 can be released through the activation of the holding and release mechanism 146 of the pushing arms 140, and finally tightened in a conventional fashion, such as pulling on the lead end 138 of the snare 130 at the handle end 110 (shown in FIG. 37). The pushing arms 140 may be configured to advance independently from each other which allows for better manipulation of the snare 130 in the deployed position. Specifically the independent movement of the arms 140 allows for an oblique (non-perpendicular) approach to the left atrial appendage, and allows for adjusting one side of the snare 130 in various applications. With the formation of the pushing arms 140 as hollow lumens, one of the pushing arms 140 can also contain the control end 138 of the snare 130 which the operator can access at the deployment control 142.

If desired, a mechanism for trimming 160 the trailing end of the snare 130 can be incorporated into the pushing arm 140 containing the control end of the snare 130. As shown in FIGS. 36-41 the control end 138 of the snare 130 may extend into the interior of the pushing arm 140 through a lateral opening and through a second lumen that forms the trimming mechanism 160, wherein the trimming mechanism 160 may further include a beveled sharp leading edge or edges which would only contact the snare 130 upon advancement of the lumen 160 past the entrance hole for trimming as shown in figures in sequential FIGS. 38-41. This trimming is performed immediately prior to removal of the apparatus 100 and after deployment of the snare 130, and with the snare 130 snugly secured to the left atrial appendage. The forward sharpened edge of the trimming mechanism can be effective to trim the snare 130 through a shearing action relative to the access hole in the arm 140. Other trimming devices can also be designed, the present mechanism 160 is simply one embodiment of an efficient, effective trimming device.

Figure 42:
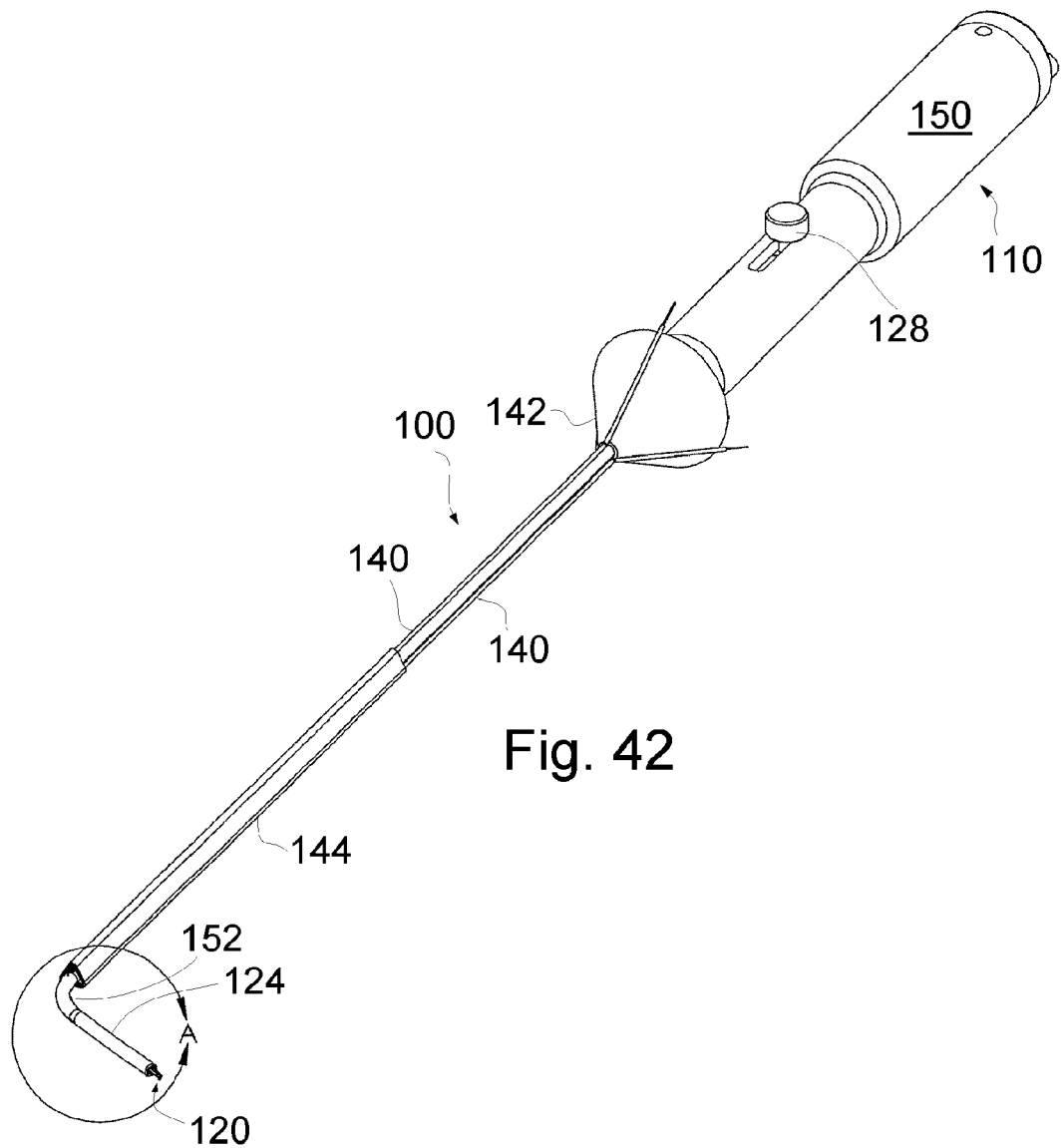
FIG. 42 is a perspective view of the integrated steer-able grasper and snare deploying medical apparatus of FIG. 1 schematically illustrating the steer-able distal end of the apparatus.
Figure 43:
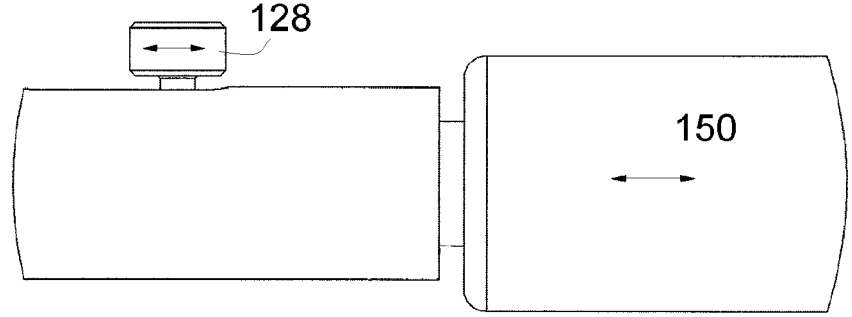

It is contemplated that the present invention is steer-able, meaning it can be guided and manipulated by the user. FIG. 42 is a perspective view of the integrated steer-able grasper and snare deploying medical apparatus 100 of FIG. 1 schematically illustrating the steer-able distal end of the apparatus 100 and FIG. 43 is an enlarged view of the operator handle end 110 of the apparatus illustrating the steering control 150 for the apparatus. Essentially a selected portion 152 of the grasper lumen 122 may be formed of a lower durometer material so that it is more flexible. A control guide wire (not shown) coupled to one side of the bendable portion 152 can extend back to an axial movable steering control 150. It will be understood that sliding the steering control 150 rearward, relative to the remainder of the apparatus 100, will cause the selected portion 152 to bend more, thereby giving a steering capability to the apparatus 100 which is simple to operate and control. The amount of bend is generally exaggerated in the figures and is for illustrative purposes. The snare 130 will follow the curved end for deployment. The degree of bend may or may not be helpful for snare 130 deployment. Additional degrees of freedom can be added through distinct bending portions with distinct bending control wires.

Figure 44:
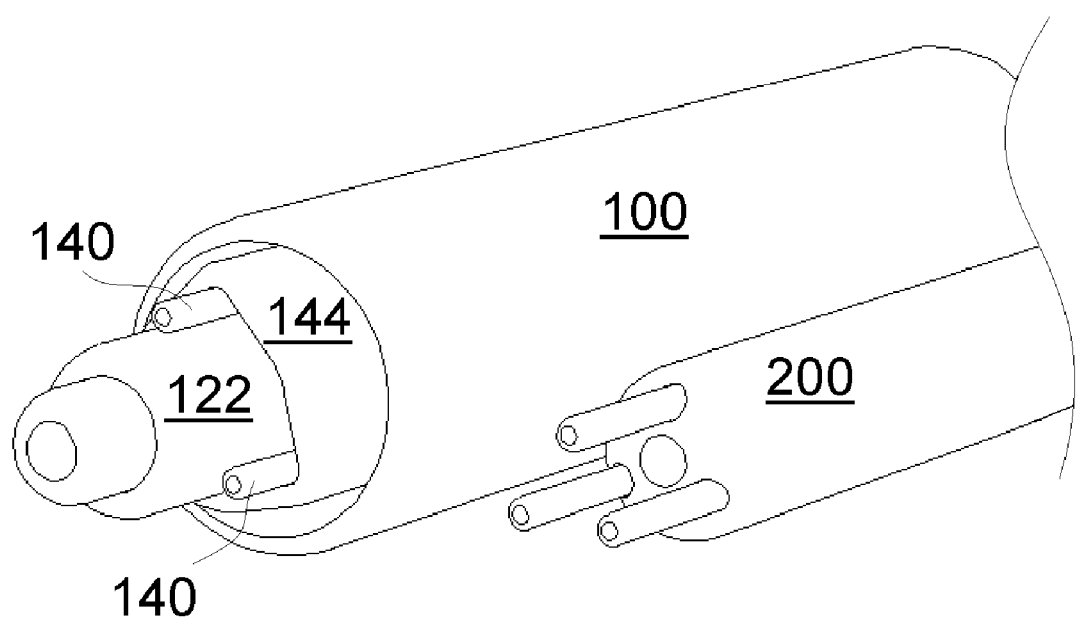
FIG. 44 is a perspective view of the medical apparatus of FIG. 1 aside a modified housing for the medical apparatus according to the present invention.

It should be apparent to those of ordinary skill in the art that various modifications may be made to the present invention without departing from the spirit and scope thereof. The described embodiments of the present invention are intended to be illustrative of the present invention and not restrictive thereof. One modification of the invention is a molded housing 200 shown in FIG. 44, as opposed to the multiple lumen design, wherein the housing 200 includes the relevant ports and easily accommodates independent operation of the pusher arms 40. A single integrated housing 200 can minimize the relative size of the device as shown in comparison to apparatus 100. FIG. 44 illustrates that significant changes can be made to the present invention without departing from the spirit and scope thereof.

Whereas particular embodiments of this invention have been described above for purposes of illustration, it will be evident to those skilled in the art that numerous variations of the details of the present invention may be made without departing from the invention as defined in the appended claims. The scope of the present invention is intended to be defined by the appended claims and equivalents thereto.

What is claimed is:

1. An integrated medical apparatus for grasping, manipulation and closure of tissue comprising:
    an operator handle end;
    a grasper lumen extending from the operator handle end;
    a grasping member having multiple prongs positioned within and movable relative to the grasper lumen;
    an axial moveable contractible snare; and
    at least one axially moveable snare pushing arm, wherein at least one pushing arm is formed as a lumen and includes a snare holding and release mechanism including at least one continuous wire extending through the pusher arm and coiled around the snare greater than 360 degrees in a single wire continuous coil when in a snare holding position and configured to be pulled through the pushing arm and be uncoiled from around the snare when moved to a snare releasing position.

2. The integrated medical apparatus for grasping, manipulation and closure of tissue according to claim 1, wherein the grasping prongs are moved between an open and closed position by relative axial movement between the prongs of the grasping member and the grasper lumen and wherein the prongs of the grasping member are formed as wire members having a memory of the open position.

3. The integrated medical apparatus for grasping, manipulation and closure of tissue according to claim 1, wherein the grasping prongs are moved between an open and closed position by relative axial movement between the prongs of the grasping member and the grasper lumen and wherein the prongs of the grasping member are wire members including gripping ends designed to maximize tissue gripping function and minimize tissue damage.

4. The integrated medical apparatus for grasping, manipulation and closure of tissue according to claim 1, wherein the grasping prongs are moved between an open and closed position by relative axial movement between the prongs of the grasping member and the grasper lumen and wherein the prongs of the grasping member are three wire members positioned approximately 120 degrees apart.

5. The integrated medical apparatus for grasping, manipulation and closure of tissue according to claim 1 wherein the snare is a looped flexible material having a slip-knot and a control end extending to the operator handle end of the apparatus.

6. The integrated medical apparatus for grasping, manipulation and closure of tissue according to claim 1 wherein the snare further includes a band of material at the loop thereof for distributing the forces of the snare as it is tightened and deployed around the tissue, whereby tissue damage is minimized.

7. The integrated medical apparatus for grasping, manipulation and closure of tissue according to claim 1 further including a sliding control knob on the handle end for opening and closing the grasping member, and wherein the grasping prongs are moved between an open and closed position by relative axial movement between the prongs of the grasping member and the grasper lumen.

8. The integrated medical apparatus for grasping, manipulation and closure of tissue according to claim 1 wherein the at least one snare pushing arm is configured to advance the snare in an open, encircling position to a final deployed position.

9. The integrated medical apparatus for grasping, manipulation and closure of tissue according to claim 8 further including a plurality of said snare pushing arms and an axially sliding pushing arm containment sleeve which is adapted to hold the pusher arms in a retracted position for insertion of the apparatus.

10. The integrated medical apparatus for grasping, manipulation and closure of tissue according to claim 9 wherein the containment sleeve is configured to slide axially rearward toward the handle end to open the snare and the pusher arms for snare deployment.

11. The integrated medical apparatus for grasping, manipulation and closure of tissue according to claim 1 wherein the at least one snare pushing arm is configured to advance the snare in an open, encircling position to a final deployed position and wherein each pushing arm is formed as a lumen and each pushing arm includes a snare holding and release mechanism formed as at least one continuous wire loop at the end of the pusher arm lumen and extending through the pusher arm lumen and coiled around the snare greater than 360 degrees in a single wire continuous coil when in a snare holding position and configured to be pulled through the pushing arm lumen and be uncoiled from around the snare when moved to a snare releasing position.

12. The integrated medical apparatus for grasping, manipulation and closure of tissue according to claim 1 further including a plurality of said axially moveable snare pushing arm, wherein at least one pushing arm includes a snare holding and release mechanism, wherein the snare pushing arms are configured to advance the snare in an open, encircling position to a final deployed position and wherein at least one of the pushing arms is a hollow lumen that contains a control end of the snare.

13. The integrated medical apparatus for grasping, manipulation and closure of tissue according to claim 1 further including a plurality of said axially moveable snare pushing arms, wherein the snare pushing arms are configured to advance the snare in an open, encircling position to a final deployed position and wherein at least one of the pushing arms includes a mechanism for trimming a trailing end of the snare following final snare deployment.

14. The integrated medical apparatus for grasping, manipulation and closure of tissue according to claim 1 wherein the apparatus is can be guided and manipulated by the user by selectively curving an end of the grasper lumen.

15. A medical apparatus for remote grasping, manipulation or release of an object comprising:
    at least one hollow lumen extending from an operator end;
    a plurality of loops for the grasping, manipulation and/or release of a desired object at spaced locations along the object, each loop formed of a wire coiled around the object greater than 360 degrees in a single wire continuous coil loop when in a holding and manipulating position and configured to be uncoiled from around the object when moved to an object releasing position; and
    a wire extending through the lumen and axially moving through the lumen, wherein a lead end of the wire extending out of a distal end of the lumen will form at least one of the loops for the grasping, manipulation and/or release of a desired object, wherein the wire has sufficient memory and is sufficiently flexible such that at least one of the loops will be selectively coiled and uncoiled as the wire is advanced and retracted relative to the lumen.

16. The medical apparatus of claim 15 wherein each of the loops is formed of at least two complete revolutions of the continuous wire forming that loop when in the holding and manipulating position.

17. The medical apparatus of claim 15 wherein a plurality of lumens and wires are provided, one wire forming each loop.

18. A medical apparatus for snaring tissue with remote manipulation and release of a snare comprising:
an operator handle end;
an axial moveable contractible snare; and
at least one axially moveable snare pushing arm formed as a lumen and including a snare holding and release mechanism which includes at least one continuous wire extending through the pusher arm and coiled around the snare greater than 360 degrees in a single wire continuous coil loop when in a snare holding position and configured to be pulled through the pushing arm lumen and be uncoiled from around the snare when moved to a snare releasing position.

19. The medical apparatus of claim 18 wherein the coiled wire loop is formed of at least two complete revolutions of the continuous wire around the snare when in the snare holding position.

20. The medical apparatus of claim 19 wherein a plurality of lumens and wires are provided, and wherein each wire has sufficient memory and is sufficiently flexible such that at least one loop will be selectively coiled as the wire is advanced relative to the lumen.

* * * * *